US007247146B2

(12) United States Patent
Tonelli et al.

(10) Patent No.: US 7,247,146 B2
(45) Date of Patent: *Jul. 24, 2007

(54) SUPPORT ELEMENT FOR AN INTEGRATED BLOOD TREATMENT MODULE, INTEGRATED BLOOD TREATMENT MODULE AND EXTRACORPOREAL BLOOD TREATMENT APPARATUS EQUIPPED WITH SAID INTEGRATED MODULE

(75) Inventors: Claudio Tonelli, Modena (IT); Vincenzo Baraldi, Quistello (IT); Massimo Zaccarelli, San Felice sul Panaro (IT); Annalisa Delnevo, Sant' Agata Bolognese (IT); Francesco Ribolzi, Modena (IT); Jacques Chevallet, Serezin du Rhone (FR); Jacques Duchamp, Bron (FR); Aziz Aberkane, Decines (FR); Gabriel Meyssonnier, Dizimieu (FR); Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 418 days.

This patent is subject to a terminal disclaimer.

(21) Appl. No.: 10/775,993

(22) Filed: Feb. 9, 2004

(65) Prior Publication Data
US 2004/0167457 A1 Aug. 26, 2004

Related U.S. Application Data

(60) Provisional application No. 60/470,453, filed on May 15, 2003.

(30) Foreign Application Priority Data
Feb. 7, 2003 (IT) .......................... MI2003A0213

(51) Int. Cl.
*A61M 37/00* (2006.01)
*A61M 1/16* (2006.01)
*F04B 43/08* (2006.01)
*B01D 63/00* (2006.01)
*F16K 1/00* (2006.01)
*C02F 1/44* (2006.01)

(52) U.S. Cl. .................... 604/4.01; 604/6.09; 604/6.11; 210/195.2; 210/645; 417/477.6; 417/477.12; 137/861

(58) Field of Classification Search ............... 604/4.01, 604/5.01, 5.04, 6.09, 6.11, 6.16; 210/645–647, 210/90, 525, 321.71, 232, 240; 422/44; 417/477.2, 417/237, 439, 472, 474, 2; 248/274.1; 312/209; 137/861
See application file for complete search history.

(56) References Cited

U.S. PATENT DOCUMENTS 3,909,045 A 9/1975 Meagher ...................... 285/22

(Continued)

FOREIGN PATENT DOCUMENTS

AU 744404 1/1999

(Continued)

OTHER PUBLICATIONS

Indian Plastic Portal Spec sheet for PETG, printed Sep. 7, 2006; http://www.indianplasticportal.com/petg.html.*

(Continued)

*Primary Examiner*—Tatyana Zalukaeva
*Assistant Examiner*—Leslie R. Deak
(74) *Attorney, Agent, or Firm*—Finnegan, Henderson, Farabow, Garrett & Dunner, L.L.P.

(57) ABSTRACT

The invention relates to support element (4) comprising a main body (6) having a front wall (25) and a peripheral wall (32) projecting away from the front wall. The front wall and the peripheral wall define a housing compartment (33) designed to receive a fluid distribution circuitry cooperating with a treatment unit for defining an integrated blood treatment module.

57 Claims, 19 Drawing Sheets

U.S. PATENT DOCUMENTS

| | | | |
|---|---|---|---|
| 4,009,107 A | 2/1977 | Miller et al. | 210/321 B |
| 4,263,808 A | 4/1981 | Bellotti et al. | 73/714 |
| 4,379,452 A | 4/1983 | DeVries | 604/6 |
| 4,424,009 A | 1/1984 | van Os | 417/394 |
| 4,436,620 A | 3/1984 | Bellotti et al. | 210/90 |
| 4,526,515 A | 7/1985 | DeVries | 417/63 |
| 4,637,813 A * | 1/1987 | DeVries | 604/6.01 |
| 4,844,810 A | 7/1989 | Richalley et al. | |
| 4,871,012 A | 10/1989 | Kuo | 165/41 |
| 4,886,431 A | 12/1989 | Soderquist et al. | 417/477 |
| 4,950,245 A | 8/1990 | Brown et al. | 604/153 |
| 5,311,908 A | 5/1994 | Barone et al. | |
| 5,427,509 A | 6/1995 | Chapman et al. | 417/477.2 |
| 5,441,636 A * | 8/1995 | Chevallet et al. | 210/232 |
| 5,462,416 A | 10/1995 | Dennehey et al. | 417/477.2 |
| 5,482,440 A * | 1/1996 | Dennehey et al. | 417/63 |
| 5,641,144 A | 6/1997 | Hendrickson et al. | 248/292.13 |
| 5,714,060 A | 2/1998 | Kenley et al. | 210/194 |
| 5,983,947 A | 11/1999 | Utterberg | 138/89 |
| 6,277,277 B1 | 8/2001 | Jacobi et al. | 210/240 |
| 6,308,721 B1 | 10/2001 | Bock et al. | 134/166 R |
| 6,325,775 B1 | 12/2001 | Thom et al. | 604/6.02 |
| 6,589,482 B1 * | 7/2003 | Burbank et al. | 422/44 |
| 2004/0158190 A1 * | 8/2004 | Duchamp et al. | 604/6.09 |
| 2004/0162513 A1 * | 8/2004 | Neri et al. | 604/6.09 |

FOREIGN PATENT DOCUMENTS

| | | |
|---|---|---|
| AU | 199870078 A1 | 1/1999 |
| AU | 199870078 B2 | 1/1999 |
| EP | 0 134 436 B1 | 1/1988 |
| EP | 0 256 956 B1 | 2/1988 |
| EP | 0 116 596 B1 | 11/1990 |
| EP | 0 282 539 B1 | 1/1992 |
| EP | 0 611 227 A1 | 8/1994 |
| EP | 0 643 808 B1 | 1/1998 |
| EP | 0 695 397 B1 | 9/1998 |
| EP | 0 887 100 A1 | 12/1998 |
| EP | 0 893 603 A2 | 1/1999 |
| EP | 0 694 125 B1 | 2/1999 |
| EP | 0 686 237 B1 | 5/1999 |
| EP | 0 992 256 A2 | 4/2000 |
| EP | 0 679 099 B1 | 7/2001 |
| EP | 0 852 953 B1 | 11/2001 |
| GB | 2 076 476 A | 12/1981 |
| GB | 2 110 564 | 6/1983 |
| GB | 2 208 896 A | 4/1989 |
| WO | WO 88/01895 | 3/1988 |
| WO | WO 95/17597 | 6/1995 |
| WO | WO 95/17598 | 6/1995 |
| WO | WO 95/17599 | 6/1995 |
| WO | WO 95/17600 | 6/1995 |
| WO | WO 95/17601 | 6/1995 |
| WO | WO 95/17602 | 6/1995 |
| WO | WO 95/17603 | 6/1995 |
| WO | WO 95/17604 | 6/1995 |
| WO | WO 97/02056 | 1/1997 |
| WO | WO 97/10436 | 3/1997 |
| WO | WO 98/22163 | 5/1998 |
| WO | WO 99/13926 | 3/1999 |
| WO | WO 01/08722 A2 | 2/2001 |
| WO | WO 01/08772 A2 | 2/2001 |
| WO | WO 02/26288 A2 | 4/2002 |

OTHER PUBLICATIONS

International Search Report of International Application No. PCT/IB2004/000105.

International Search Report for International Application No. PCT/IB2004/000104.

\* cited by examiner

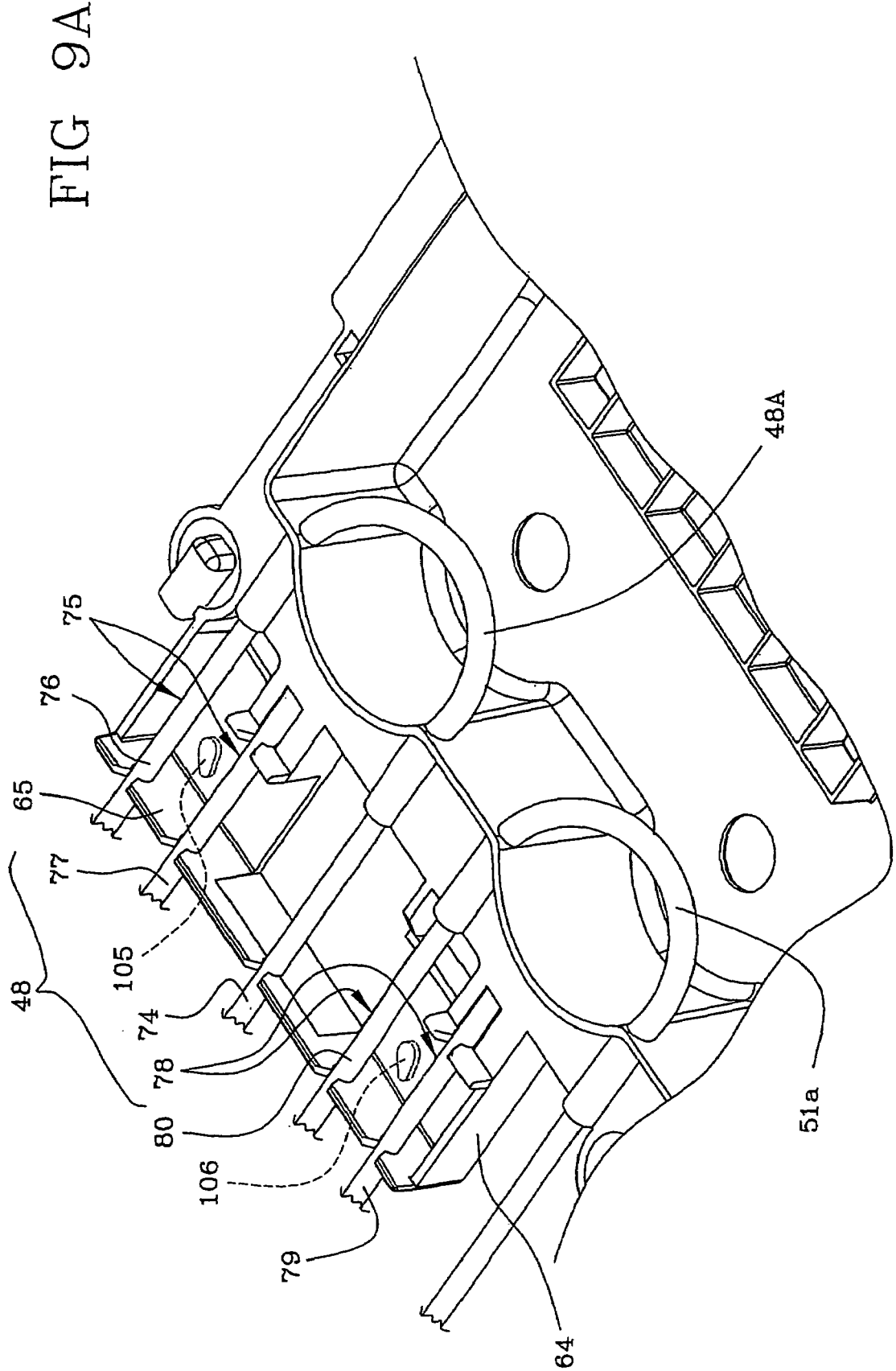

US 7,247,146 B2

SUPPORT ELEMENT FOR AN INTEGRATED BLOOD TREATMENT MODULE, INTEGRATED BLOOD TREATMENT MODULE AND EXTRACORPOREAL BLOOD TREATMENT APPARATUS EQUIPPED WITH SAID INTEGRATED MODULE

Applicants claim the right to priority based on Italian Patent Application No. MI2003A000213, filed Feb. 7, 2003, in Italy and U.S. Provisional Patent Application No. 60/470,453, filed May 15, 2003.

BACKGROUND OF THE INVENTION

The present invention relates to a support element, to an integrated blood treatment module comprising said support element and to an extracorporeal blood treatment apparatus equipped with said integrated module.

As is known, in order to carry out extracorporeal blood treatments such as for instance haemodialysis, haemofiltration, haemodiafiltration, plasmapheresis, extracorporeal blood oxygenation, extracorporeal blood filtration or other treatments, it is necessary to provide for at least an extracorporeal circuit through which the blood flows and is conveyed towards a treatment unit; the treated blood is then carried back to the patient's cardiovascular system. Referring by way of example to a dialysis treatment, the extracorporeal circuit used comprises: a dialysis filter consisting of a housing body defining at least a first and a second chamber separated from each other by a semipermeable membrane, a blood withdrawal line leading to the first chamber of the dialysis filter and a blood return line designed to receive blood coming out of the first chamber and to carry it back to the patient. The second chamber of the dialysis filter is then connected to a circuit for the circulation of a dialysis liquid designed to receive the impurities that are present in the blood and the excess fluid that has to be removed from the patient's blood.

Currently, in apparatus for extracorporeal blood treatments all the lines designed for the circulation of the dialysis liquid are housed within the dialysis apparatus, whereas the lines constituting the extracorporeal blood circuit are replaced at every treatment and suitably connected to the dialysis filter, which can be replaced either at every treatment or from time to time, as required.

From a structural point of view the dialysis filter, the lines for the circulation of the dialysis liquid and the lines constituting the withdrawal and return branch carrying the blood back to the patient consist of separate parts that are connected and cooperate during operation after being suitably assembled.

There are also apparatuses that are available on the market at present, designed in particular for intensive treatment of kidney failure, which are advantageously equipped with integrated modules comprising a support structure, a dialysis filter engaged to the support structure by means of a suitable support projecting from said structure, as well as a hydraulic circuit comprising the tubes that are necessary to define the blood withdrawal and return lines leading to the patient, the possible lines for the infusion of anticoagulant or substitution liquids, the intake line for the dialysis liquid and the discharge line for the liquid coming out of the second chamber of the dialyser.

The integrated modules described above enable an easy and immediate association of the lines to the treatment apparatus and do not require any connection between the treatment unit, such as for instance a dialysis filter, and the various tubes or lines designed to convey blood and other fluids. Moreover, said integrated modules enable the removal both of the tubes conveying the blood and of the tubes conveying other fluids at the end of the treatment. In other words, thanks to a simple loading and connecting operation of the terminals and of the fluid conveyance lines to the corresponding sources such as bags or others, the user can install a dialysis apparatus. Analogously, once the treatment step is over, by simply disconnecting and disassembling the integrated module from the blood treatment apparatus in few operations, the operator can completely disassemble both the extracorporeal circuit and the blood treatment unit, as well as the tubes for the circulation of possible infusion liquids and of the dialysis liquid. The easy installation of said modules ensures an efficiency and a speed that are certainly advantageous for intensive treatments where the personnel, who might not be conversant with the use of blood treatment apparatuses, can thus operate rapidly and with a high reliability.

From a structural point of view treatment modules consist of a support element to which the fluid distribution circuitry and the blood treatment unit are suitably fastened.

The support element can have different shapes and geometries according to the type and model of integrated module; in particular, it is known about a first arrangement in which the support element is basically defined by a quadrangular plate to which respective tube lengths are fastened by means of suitable engagement connectors, and which also supports the filter directly in its central portion by means of an auxiliary support structure.

The tubes of the fluid circuitry engaged laterally with respect to the support element define suitable tube lengths basically shaped as a U and projecting away from the respective sides. Said U-shaped tube lengths are designed to be associated to respective peristaltic pumps for conveying fluids therein.

It is also known about a further embodiment of an integrated module, in which a support element is designed to keep basically U-shaped respective tube lengths in position and carries a filter suitably engaged thereto.

The support element is defined by a quadrangular frame completely open on two opposite sides and consisting of respective consecutive sides having the U-shaped tube lengths, which are housed within said frame.

However, the integrated modules that are present and widely spread today on the market have proved to be susceptible of several improvements.

In particular, it should be noted how the tube lengths that are designed to cooperate with the respective peristaltic pumps are generally easily accessible by the operator.

In other words, especially when the apparatus is working, the various parts that are moving (generally the peristaltic pumps) are placed in the front of the apparatus, thus enabling possible unwanted bodies to get near the moving parts by chance and to interfere with the good working of said pumps; also the operators can come into unintentional contact with the moving pumps.

Furthermore, said support elements have proved to be improvable as far as their constructive geometry is concerned, in order to improve the centering and the engagement to the front wall of the blood treatment apparatus; said element, have eventually proved to be susceptible of changes also as far as the particular relative arrangement of the various components and their overall dimensions and compactness are concerned.

SUMMARY OF THE INVENTION

The present invention therefore aims at solving basically all the drawbacks referred to above.

A first aim of the invention is to provide for a support element and a corresponding integrated module with an easier installation, which also enable a suitable protection when the machine is working, from and of the moving parts of said machine by preventing a direct access to the pumps.

Obviously, the modules according to the invention keep assembling operations extremely simple and rapid to be carried out.

A further aim of the invention is to enable an optimal arrangement of the tube lengths on the pumps and to ensure an optimal and firm engagement of the module to the machine.

Auxiliary aims of the present invention are then to enable the implementation of extremely compact integrated modules with such an arrangement of the tube lengths as to minimize the amount of dialysis fluid to be used and to minimize the amount of blood circulating outside the patient.

These and other aims, which shall be evident in the course of the present description, are basically achieved by a support element, by an integrated module and by a machine as described in the appended claims.

Further characteristics and advantages will be clearer from the detailed description of a preferred though not exclusive embodiment of a support element, of an integrated module and of a corresponding machine for extracorporeal blood treatment according to the present invention.

BRIEF DESCRIPTION OF THE DRAWINGS

This description will be given below with reference to the appended drawings, which are provided as a mere guidance and are therefore not limiting, in which:

FIG. 9a shows an enlarged detail of the module of FIG. 9;

DETAILED DESCRIPTION

Figure 1:
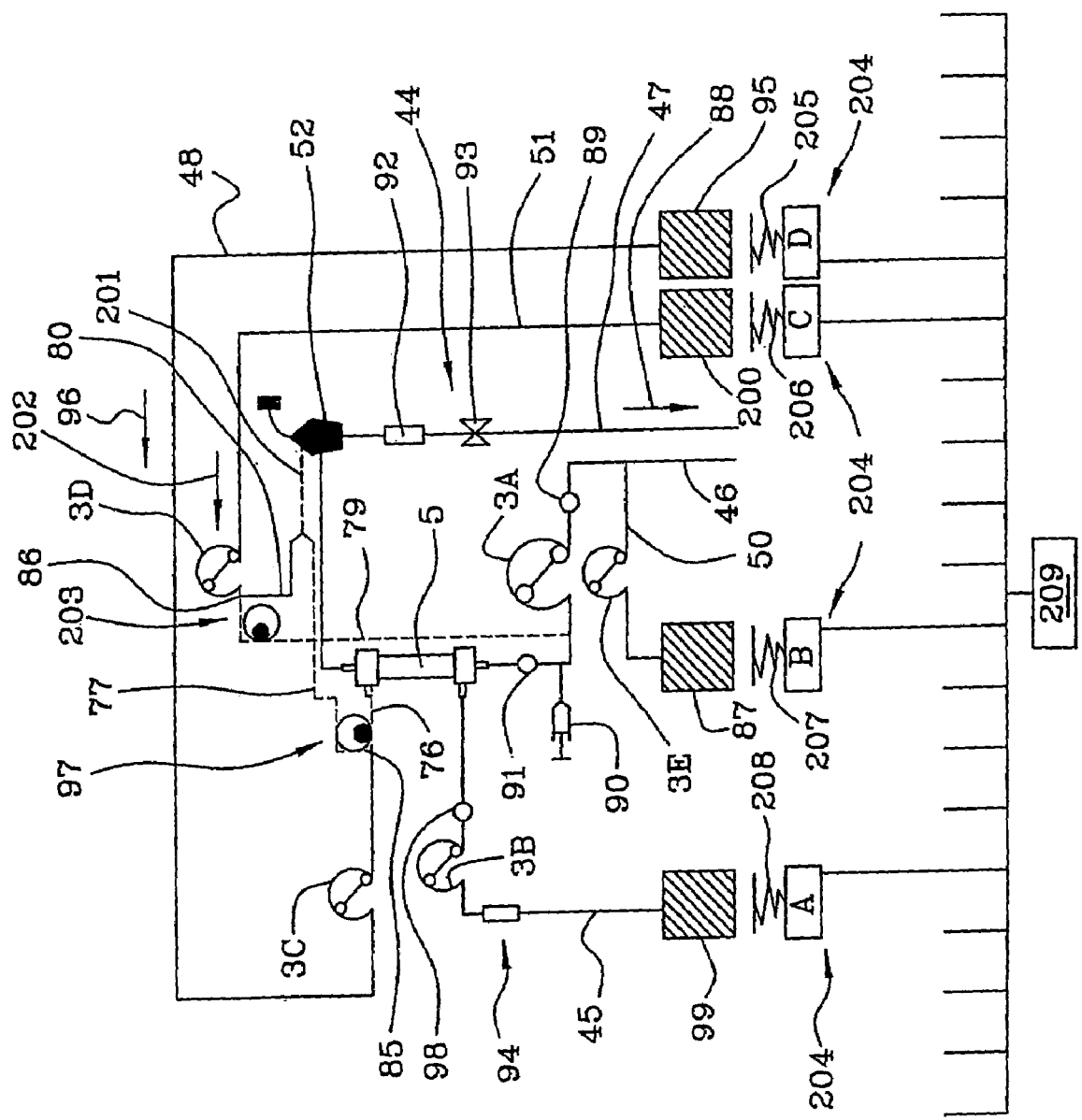
FIG. 1 shows a schematic view of a hydraulic circuit carried out by an apparatus and a module according to the present invention.

With reference to the figures mentioned above the numeral 4 globally refers to a support element according to the present invention.

Conversely, the numeral 1 refers to an integrated module (combination of a support element 4, a distribution circuitry 15 and a blood treatment unit 5) that can be used together with extracorporeal blood treatment machines 2 according to the present invention.

As can be inferred from the appended Table 1, the global hydraulic circuit carried out thanks to the cooperation between the integrated module and the machine consists of a blood line or circuit 44, which takes blood from a patient, for instance by means of a catheter introduced into a vein or artery of said patient, and through at least a withdrawal branch or inlet line 46 carries said blood, for instance continuously, to a filtration unit 5.

Then the blood passes through a primary chamber of said filtration unit 5 and through an outlet line 47 the treated blood is carried back to the patient.

The connection with an auxiliary pre-infusion line 50 is provided immediately downstream from the blood collecting zone on the inlet line 46.

In particular, the machine is equipped with at least a secondary fluid container or bag 87 for supplying the preinfusion line 50; by using corresponding means for conveying fluid, in the example shown comprising an auxiliary preinfusion pump 3e, for instance a peristaltic pump, it is possible to control the fluid flow within said line by introducing said fluid directly into the blood by means of a direct connection to the inlet line 46.

Generally, the secondary fluid container 87 can house a suitable biological fluid for a pre-infusion, however said bag 87 can also contain an anticoagulant, generally of a topical nature so as to ensure a particular working of the machine as shall be explained below in further detail.

After defining a direction of blood circulation 88 from the inlet line 46 towards the filtration unit and from the latter through the outlet line 47 towards the patient, a known blood pressure sensor 89, which shall not be described in further detail, is placed immediately downstream from the auxiliary pre-infusion line 50.

The blood circuit 44 therefore comprises means-for conveying fluid, i.e. in this particular case at least a blood pump 3a for controlling and managing the suitable blood flow in the circuit.

Also the blood pump 3a is generally a peristaltic pump.

Following the direction of blood circulation 88, there is then a device 90 for administering an anticoagulant, for instance a syringe containing suitable doses of heparin.

The blood then passes through another pressure sensor 91 controlling the correct flow within the blood circuit.

After passing through a main chamber of the filtration unit 5, where the suitable exchanges of substances, molecules and fluids occur by means of a semipermeable membrane, the treated blood enters the outlet line 47 first passing through a gas separating device (generally air) 52 commonly known as "bubble trap", designed so as to ensure the removal of air bubbles present in the blood or introduced into the blood during treatment.

The treated blood getting out of the separating device 52 then passes through an air bubble sensor 92 verifying the absence of said dangerous formations within the treated blood that has to be re-introduced in the patient's blood circulation.

Immediately downstream from the bubble sensor 92 there is an element 93 which, in case of alarm, can block the blood flow towards the patient.

In particular, should the bubble sensor 92 detect the presence of anomalies in the blood flow, the apparatus through the element 93 (be it a tap, a clamp or similar) would be able to block immediately the passage of blood so as to avoid any consequence to the patient.

Downstream from said element 93 the treated blood is then carried back to the patient undergoing therapy.

The extracorporeal blood treatment apparatus shown above is then equipped with a fluid circuit 94, which is also provided with at least an inlet line 48 leading into the filtration unit 5 and with an outlet line 45b from the filtration unit.

At least a primary fluid container 95 is designed to supply the inlet line 48 of the fluid circuit 94 (generally the primary fluid container 95 shall consist of a bag containing a suitable dialyzing liquid).

The inlet line 48 then comprises means for conveying fluid such as a least a pump 3c (in the embodiment shown a peristaltic pump) for controlling the flow of liquid from the bag 95 and for defining a direction of circulation 96.

Downstream from the pump 3c in the direction of circulation 96 there is a branching 85 splitting the fluid circuit 94 up into an intake branch 76 and into an infusion branch 77.

In particular, the infusion branch 77 is connected to the outlet line 47 of the blood circuit 44.

In other words, by means of said infusion branch 77 it is possible to obtain a post-infusion directly in the blood line using the content of the primary fluid container 95.

Conversely, the intake branch 76 conveys the fluid directly to the filtration unit and in particular to a secondary chamber of said unit.

The fluid circuit 94 is further equipped with selecting means 97 for determining the percentages of fluid flow within the infusion branch 77 and the intake branch 76.

Generally said selecting means 97, usually placed near the branching 85, can be positioned at least between a first operating condition in which they allow the passage of fluid in the intake branch 76 and block the passage in the infusion branch 77, and a second operating condition in which they allow the passage of fluid in the infusion branch 77 and block the passage in the intake branch 76.

In other words, said selecting means 97 can consist of a valve element operating on the fluid circuit 94 by alternatively blocking the passage of fluid in either branch.

It is also evident that it might be provided for suitable selectors, which are able to establish a priori the amount of liquid that has to pass through both branches simultaneously.

It will also be possible to vary the percentages of fluid in either branch as a function of time and of the preestablished therapies.

The dialysis liquid through the intake branch 76 gets into a secondary chamber of the filtration unit 5.

In particular, the primary chamber through which the blood flow passes is separated from the secondary chamber through which the dialysis liquid passes by means of a semipermeable membrane ensuring the suitable passage of the dangerous substances/molecules and of fluid from the blood towards the dialysis liquid mainly by means of convection and diffusion processes, and also ensuring through the same principles the passage of substances/molecules from the dialyzing liquid towards the blood.

The dialysis fluid then gets into the outlet line 45 and passes through a suitable pressure sensor 98 whose function is to control the working of said line.

There are then means for conveying fluid, for instance a suction pump 3b controlling the flow in the outlet line 45 within the fluid circuit 94.

Also said pump will generally be a peristaltic pump.

The fluid to be eliminated then passes through a blood detector and is conveyed into a collection container or bag 99.

Further analyzing the peculiar circuit of the apparatus according to the invention, note the presence of at least another infusion line 51 acting on the outlet line 47 of the blood circuit 44.

In particular, the infusion fluid is taken from at least an auxiliary container 200 and is sent directly to the outlet line 47 of the blood circuit 44 through means for conveying fluid, generally an infusion pump 3d controlling its flow (in the example a peristaltic pump).

In particular and as can be observed in the appended figure, the infusion liquid can be introduced directly into the gas separating device 52.

As can also be inferred, the infusion branch 77 of the fluid circuit 94 and the infusion line 51 are equipped with a common end length 201 letting into the blood circuit 44.

Said intake end length 201 is placed downstream from the infusion pump 3d with respect to a direction of infusion 202 and carries the fluid directly into the bubble trap device 52.

Further referring to the diagram in FIG. 1, note the presence within the infusion line 51 of at least a pre-infusion branch 79 connected to the inlet line 46 of the blood circuit 44.

In further detail, downstream from the infusion pump 3d with respect to the direction of infusion 202, there is a branching 86 splitting the infusion line 51 up into pre-infusion branch 79 and post-infusion branch 80.

The pre-infusion branch 79, in particular, carries the fluid taken from the bag 200 on the inlet line 46 of the blood circuit downstream from the blood pump 3a with respect to the direction of circulation 88.

Conversely, the post-infusion branch 80 is connected directly to the common end length 201.

The infusion line 51 further comprises selecting means 203 for determining the percentage of liquid flow to be sent to the post-infusion branch 80 and to the pre-infusion branch 79.

The selecting means 203 placed near the branching 86 can be positioned between at least a first operating condition in which they allow the passage of fluid in the pre-infusion branch 79 and block the passage in the post-infusion branch 80, and at least a second operating condition in which they allow the passage of fluid in the post-infusion branch 80 and block the passage in the pre-infusion branch 79.

Obviously, as in the case of the selecting means 97 present on the fluid circuit 94, also the other selecting means 203 will be able to determine the percentage of fluid that has to pass in each of the two branches and to possibly vary it in time in accordance with the planned therapies. Moreover, the selecting means 97 and the other selecting means 203 will generally though not necessarily be of the same nature.

The apparatus is then equipped with means 204 for determining at least the weight of the primary fluid container 95 and/or of the auxiliary fluid container 200 and/or of the secondary fluid container 87 and/or of the collection container 99.

In particular, said means 204 comprise weight sensors, for instance respective scales 205, 206, 207, 208 (at least an independent one for each fluid bag associated to the apparatus).

In particular, there will be at least four of said scales, each one being independent from the other and measuring the respective weight of a bag.

It should then be pointed out that there is a processing unit or CPU 209 acting on the blood circuit 44 and in particular on the pressure sensor 89, on the blood pump 3a, on the device 90 for heparin infusion, on the other pressure sensor 91, and on the device for detecting the presence of air bubbles 92 and on its respective closing element 93.

Said CPU 209 has also to control the fluid circuit 94 and, in particular, shall be input with the data detected by the scales 205 and concerning the weight of the bag 95 and shall act on the pump 3c, on the selecting means 97, on the pressure sensor 98, then on the suction pump 3b and shall eventually receive the data detected by the scales 208 whose function is to determine the weight of the collection container 99.

The CPU 209 shall also act on the infusion line 51 checking the weight of the auxiliary container 200 (checked by the scales 206) and will be able to control both the infusion pump 3d and the other selecting means 203.

Eventually, the CPU 209 shall also act on the auxiliary pre-infusion line 50 detecting the weight of the secondary fluid container 87 by means of the scales 207 and suitably controlling the pump 3e according to the treatments to be carried out.

Reminding that the above description has been made with the sole purpose of describing the whole of the hydraulic circuit of the extracorporeal blood treatment apparatus, here is a short description of the working of the device.

Once the whole hydraulic circuit and the filtering unit 5 have been correctly associated to the apparatus so that the various peristaltic pumps engage the respective lengths of tubes and that all the sensors have been suitably positioned, and the various bags containing the various fluids have been associated to the corresponding liquid intake/suction lines, and the blood circuit has been connected to a patient's artery/vein, the initial circulation of blood within its circuit is enabled.

Therefore, according to the kind of therapy that has been set, the extracorporeal blood treatment apparatus is automatically started and controlled by the processing unit 209.

If the patient undergoes an ultrafiltration treatment, beyond the blood circuit the suction pump 3b connected to the outlet line of the fluid circuit 94 is started, so as to take by convection through the filtration unit a fluid excess in the patient (beyond the dangerous substances/molecules).

Conversely, if the therapy that has been set comprises a haemofiltration treatment, beyond the blood circuit and the suction pump 3b for taking fluids by convection also the pump 3c on the inlet line of the fluid circuit 94 and the selecting means 97 placed so as to enable a post-infusion are started.

Also the infusion line 51 shall be used so as to enable a further addition of liquids to the post-infusion or to enable a suitable pre-infusion.

Conversely, if the treatment involves haemodialysis, the pumps 3c and 3b of the fluid circuit 94 shall be started and the selecting means 97 shall be positioned so as to ensure the passage of the dialysis liquid only towards the filtration unit 5 so as to take substances and/or molecules and/or liquids by diffusion and possibly by convection if the transmembrane pressure through the filtration unit is other than zero.

Eventually, if a haemodiafiltration treatment has to be carried out, beyond the blood circuit the fluid circuit and therefore the pumps 3c and 3b shall be started, so as to ensure a circulation of the liquid within the filtration unit 5 and also the pump 3d of the infusion line 51 shall be started so as to ensure a pre- or post-infusion.

Obviously, it will be possible to set up different therapies comprising one or more of the treatments referred to above.

In all the treatments described above, possibly except the ultrafiltration treatment, it will be possible to use the auxiliary pre-infusion line for introducing an anticoagulant and/or a suitable infusion liquid into the blood.

Obviously, the anticoagulant can also be administered by means of the suitable device 90 designed for the introduction of heparin into blood.

Concerning this it should be pointed out that the machine according to the invention is designed to receive various kinds of syringes according to the amount of anticoagulant to be administered.

Obviously, it is the control unit 209 that, being connected to the various devices, sensors, pumps and being input with the data on weight from the various scales, is able—once it is set—to control and automate the whole working of the apparatus.

In further detail, it is possible to set the flows of the various pumps present on the machine in accordance with the therapy or therapies to be started. Obviously, the suitable setting of said flows results in an amount of fluid taken from the patient (weight loss), which will generally be given by the difference between the weight of the liquid that has been collected in the bag 99 and of the liquid circulated in the circuit through the primary fluid container 95, the auxiliary fluid container 200 and the secondary fluid container 87.

In particular, in accordance with the data received by the control unit coming from the various scales (and the theoretical flow rates fixed on each pump of therapy/treatment carried out) the control unit 209 shall control the means for circulating fluid in the various lines by suitably varying the thrust exerted by the various pumps 3a, 3b, 3c, 3d, 3e.

In particular, the signals coming from the scales referred to above 205, 206, 207, 208 are used by the control unit 209 for determining the weight of the particular fluid introduced into the line or collected.

In order to determine the amount of fluid released or collected in a particular bag or container the control unit 209 compares at regular intervals (the greater the flows the smaller the intervals) the actual weight of the container with the desired weight (which is a direct function of the desired flow for each pump and of the time interval between each control step $\Delta W = Q \, \Delta t$).

The desired weight can be calculated as a function of the required flow (stored in a suitable storage unit of the computer) and of the time elapsed from the beginning of the treatment.

If the actual weight and the desired weight differ from each other, the control unit acts on the corresponding pump so as to reduce, and possibly cancel, said difference. In other words, during each cycle not an absolute weight variation, but only the variation in the time interval is taken into consideration to correct the latter.

The control unit takes into consideration variations in the difference starting from the last comparison, so as to avoid oscillations of the actual flow around the desired flow.

After the above description of the hydraulic circuit and of the possible working of the apparatus according to the invention incorporating said circuit, here is shown a detailed structure of the support element 4 according to the invention.

The support element as shown in the FIGS. 2 to 8a generally consists of a main body 6 and of a support structure 64 associated to said main body 6 and placed laterally with respect to the latter.

The main body 6 has a front wall 25 which is generally, though not necessarily, plane; then there is at least a peripheral wall 32 projecting away from the front wall 25 so as to define with the latter a housing compartment 33 designed to receive at least a portion of a fluid distribution circuit 15 to be associated to said support element.

Figure 2:
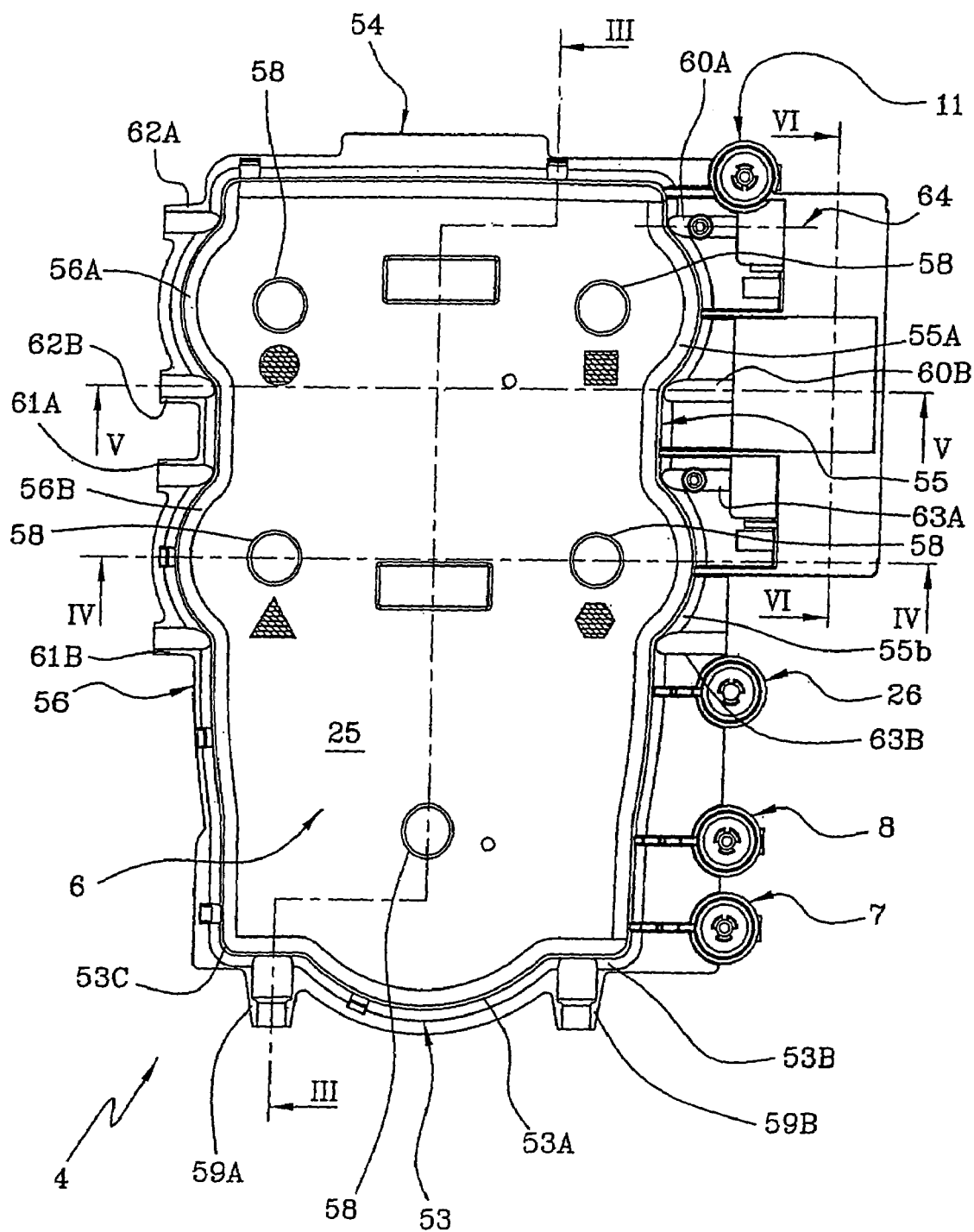
FIG. 2 shows a view from above of a support element according to the present invention.

As can be seen from FIG. 2, the front wall 25 is delimited by a given number of sides 53, 54, 55 and 56, and the peripheral wall 32 projects away from each of said sides.

It should be noted that the sides referred to above are basically rectilinear and, generally, at least first sides 55, 56 and at least second sides 53, 54 can be identified, which are basically parallel and facing each other.

In other words, in a view from above the support element 4 has an approximately quadrangular shape and its front wall 25 is delimited by first opposite longer sides 55, 56 with a basically rectilinear development and having each two curved portions 55a, 55b; 56a, 56b whose cavities face their respective opposite side.

In further detail each of said curved portions 55a, 55b; 56a, 56b can be defined by an arc of circle.

Then there are second opposite shorter sides 53, 54, whose development is again basically rectilinear; at least one of said second sides 53, 54 has a curved portion 53a placed between two rectilinear lengths 53b, 53c, which has in its turn a cavity facing the opposite side.

Here again the curved portion 53a can be defined by an arc of circle.

As can be further noted by simply observing FIG. 2, the arc of circle defining the curved portion 53a has a greater radius of curvature than the curved portions 55a, 55b, 56a, 56b defined on the first opposite longer sides 55, 56, as shall be better explained later.

Examining now the peripheral wall 32 (see FIGS. 7 and 8), it can be noted that it has at least a portion projecting away from each of the sides of the support element 4.

Generally, there will be at least one portion projecting from the first opposite sides 55, 56, and one projecting away from each of the second opposite sides 53, 54.

It is also evident that the peripheral wall 32 can also be discontinuous, i.e. it can have cavities or interruptions provided that it globally enables to define the aforesaid housing compartment 33.

Figure 7:
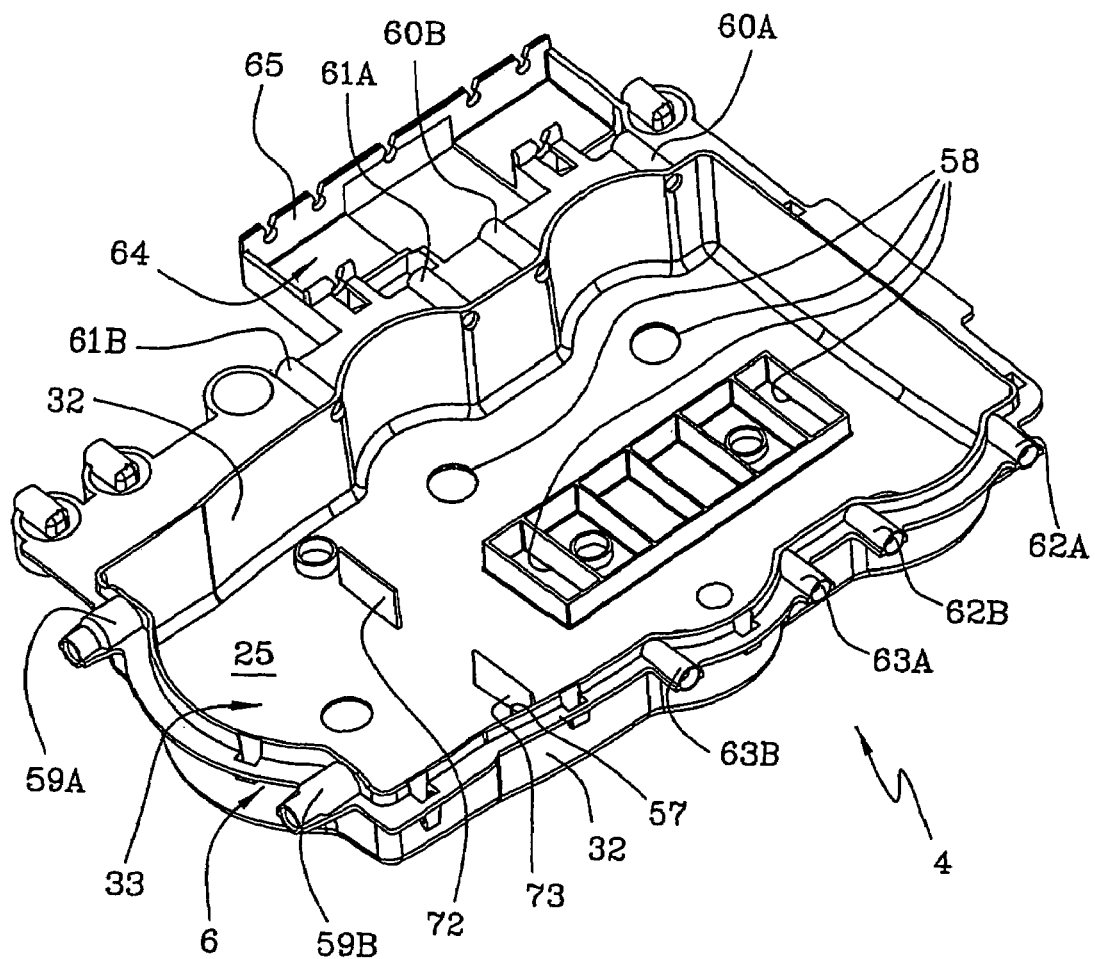
FIG. 7 shows a perspective view from a first side of the support element of FIG. 2.
Figure 8:
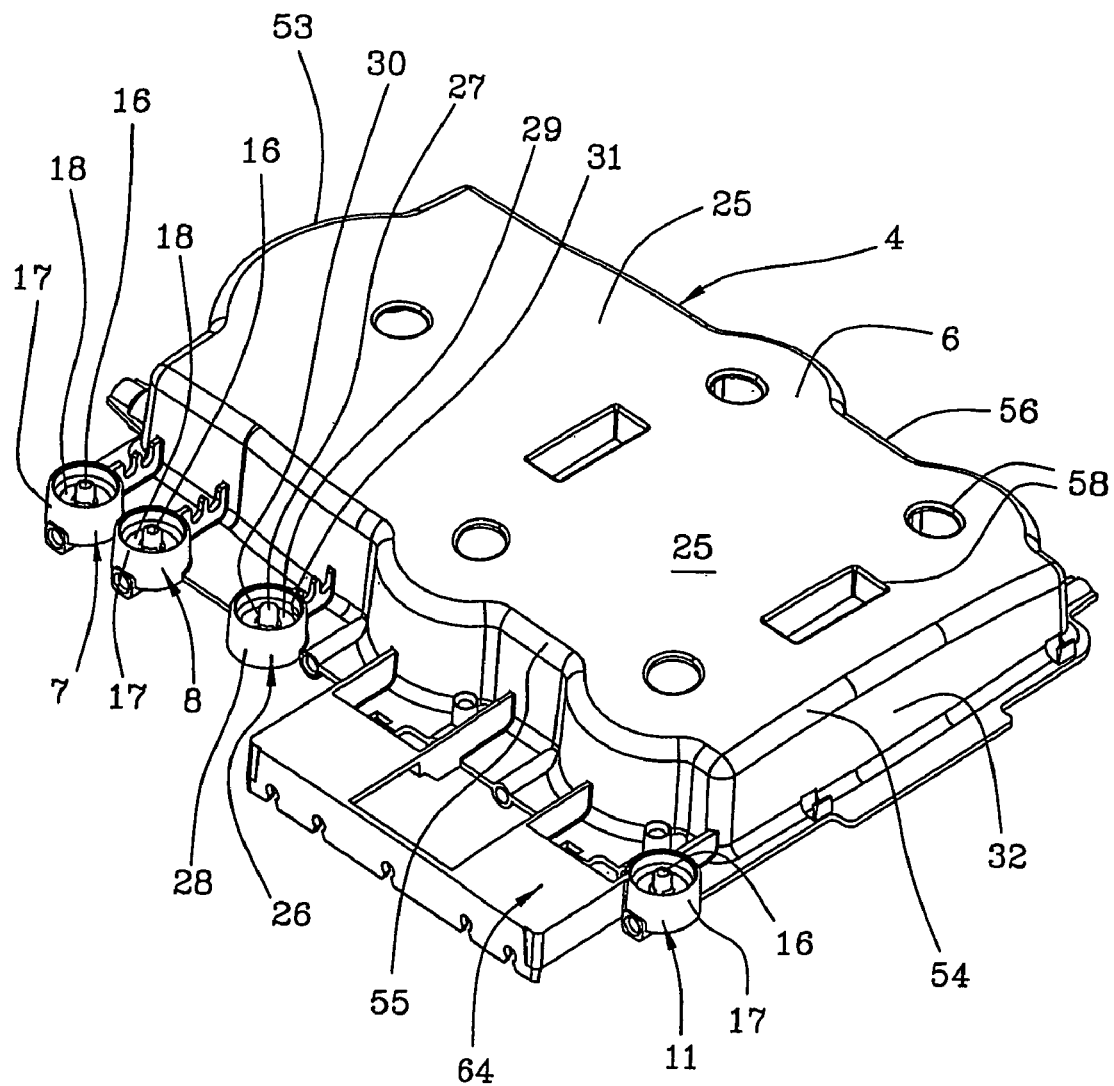
FIG. 8 shows a perspective view from the opposite side of the support element of FIG. 7.

The embodiment shown in FIGS. 7 and 8 is characterized in that the peripheral wall 32 projects away from all the sides of the front wall 25 and defines a basically continuous surface delimiting the housing compartment 33.

In other words, the housing compartment 33 has an access opening 57 without any kind of closing wall, which access opening is designed to face—when the support element 4 is being used—the extracorporeal blood treatment machine 2.

Figure 3:
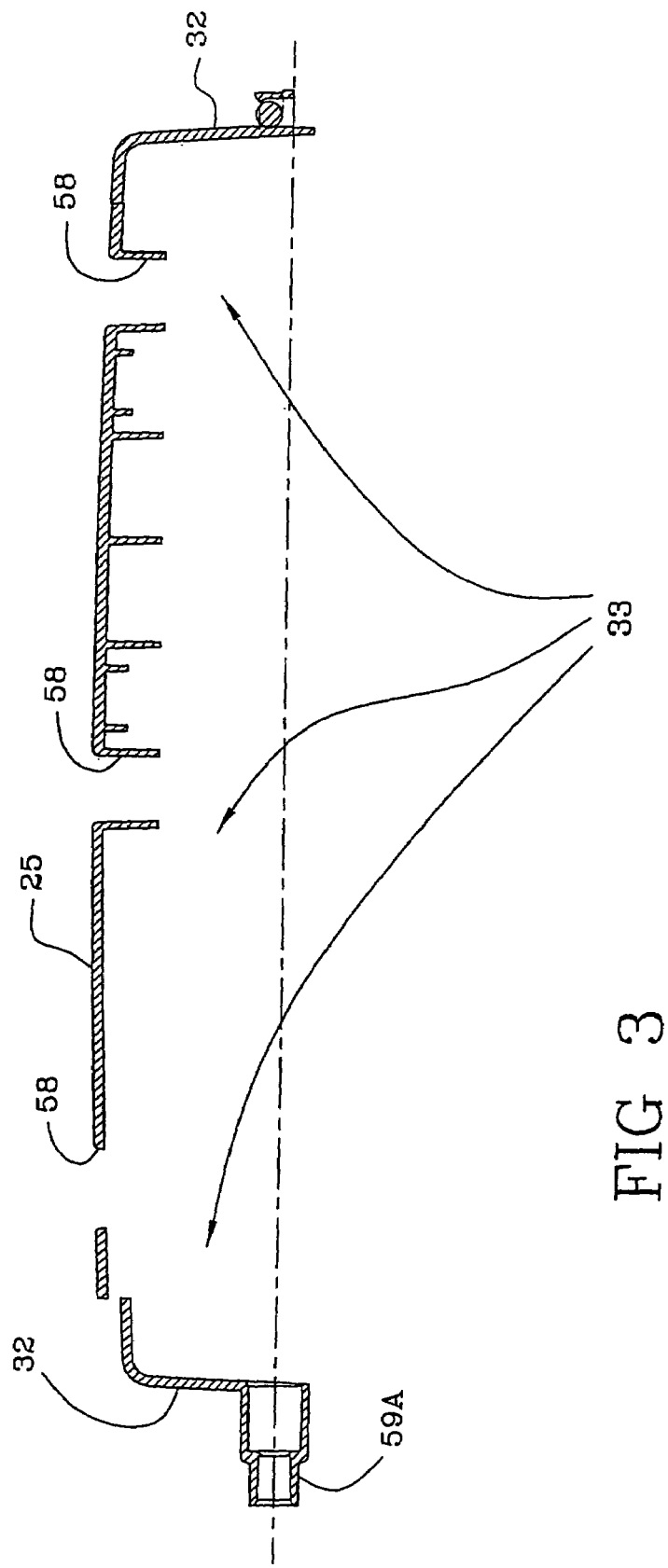
FIG. 3 shows a section of the module of FIG. 2 according to line III—III.
Figure 4:
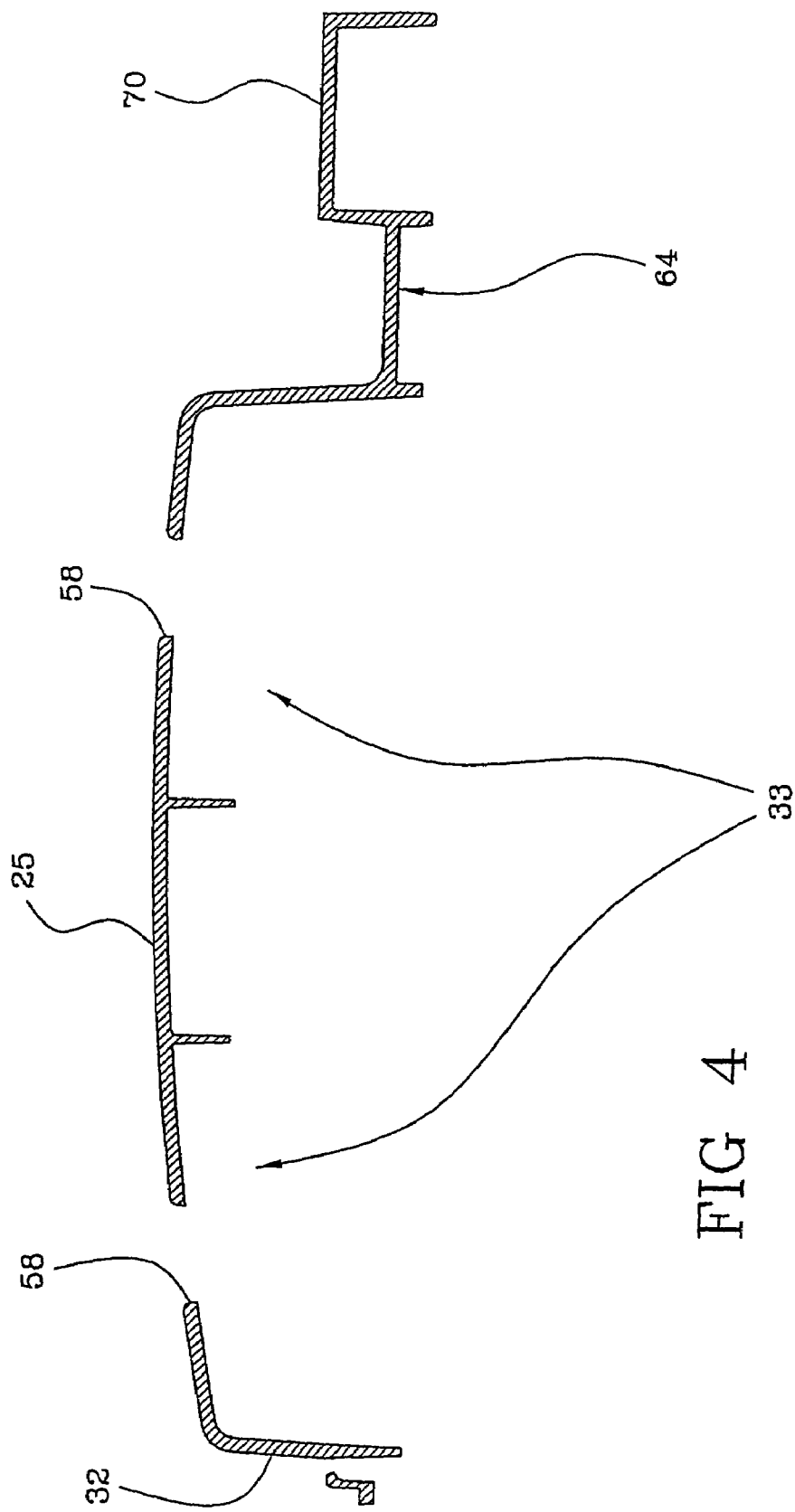
FIG. 4 shows a further section of the element of FIG. 2 according to line IV—IV.
Figure 5:
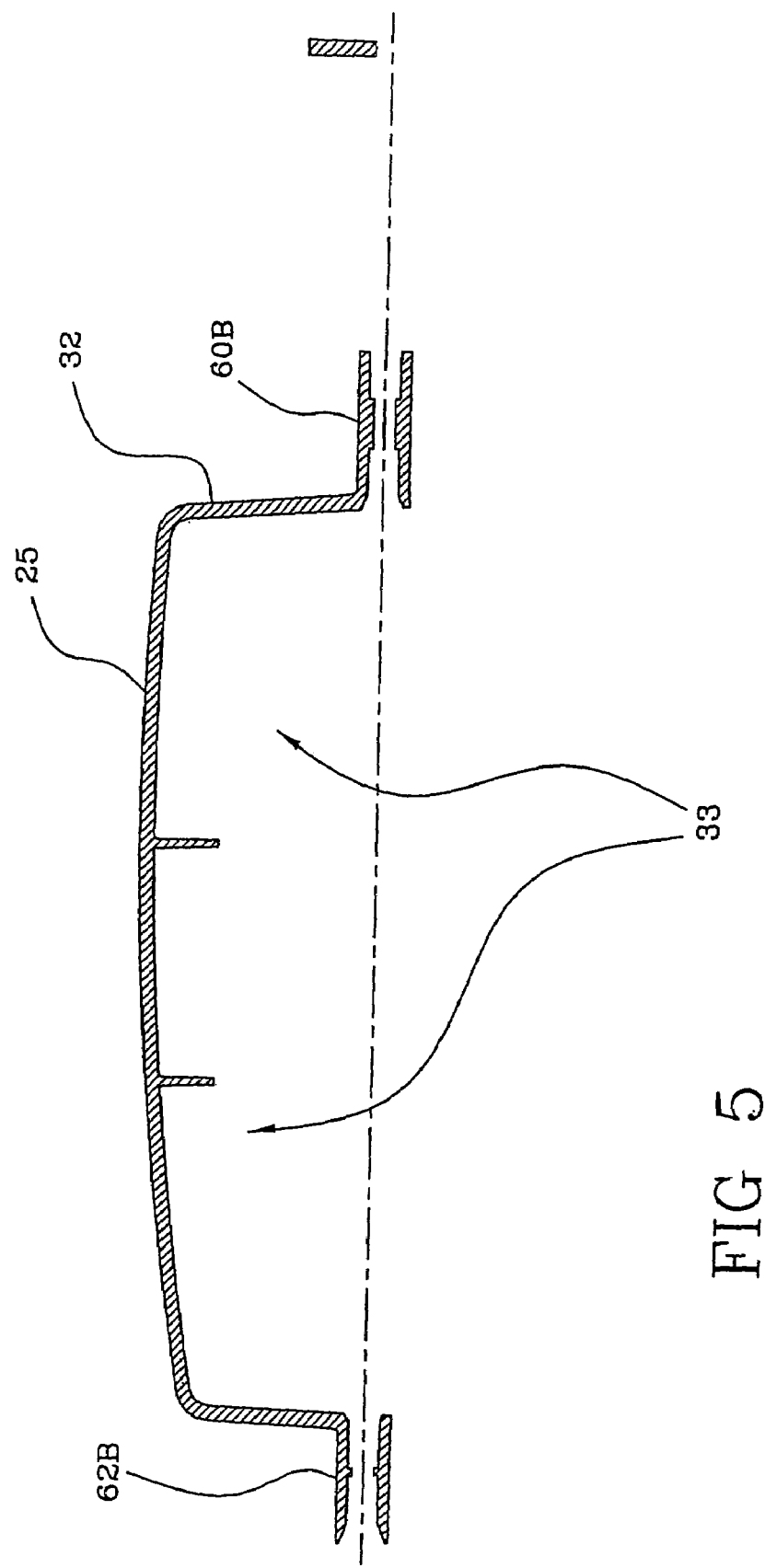
FIG. 5 shows again a section according to line V—V of FIG. 2.

Moreover, from FIGS. 3, 4, 5 it can be inferred how sections according to a plane transversal with respect to the front surface, and in particular sections according to planes orthogonal to said front surface 25, show that the main body has a substantially C-shaped profile.

The peripheral wall 32 defines the two end lengths of said C, whereas the front wall 25 defines the elongated length between said two lengths.

It should be noted how the front wall 25 and the peripheral wall 32 define a main body 6 having a box-shaped structure basically closed on five out of its six faces.

Said arrangement results in that, however sectioning the support element 4 according to two planes orthogonal one to the other and transversal to the front surface 25, the main body 6 will have C-shaped sections that are also orthogonal one to the other.

See in particular for instance the sections of FIGS. 3 and 4.

In still other words, the support element 4 comprises a front wall 25 which is able to connect opposite peripheral walls projecting in a basically perpendicular direction from said front wall 25.

As shown in FIGS. 2, 7 and 8, the front wall 25 has a given number of through openings 58 putting into communication the housing compartment 33 with the outside environment while the support element is being used.

Referring in particular to the figures described above, it can be noted that there is at least an opening 58 on each of the curved portions 53a, 55a, 55b, 56a and 56b and that said openings are defined by concentric round holes placed on the same axis as the respective arcs of circle defining the curved portions.

As far as the materials used are concerned, it should only be pointed out that the main body will be made of a stiff material, plastic for instance, which can protect the various tube lengths and/or elements therein contained.

It is also possible to carry out the whole support element or only a part of it with a material that is also transparent so as to obtain a visual access to the housing compartment 33.

Going into deeper structural details and referring in particular to FIG. 7, it can be noted that there are several engagement connectors fastened to the respective sides of the box-shaped body.

In particular, there are at least a first and a second engagement connector 59a, 59b placed laterally with respect to the curvilinear length 53a of one of said second sides 53.

Said connectors shall be secured and generally carried out as one piece with said rectilinear lengths 53b and 53c.

There are also pairs of engagement connectors 60a, 60b, 61a, 61b, 62a, 62b, 63a, 63b respectively engaged near each of the curved portions 55a, 55b, 56a, 56b of the first longer sides 55, 56.

In other words, there will be two of said connectors placed exactly on opposite ends of each of the curved portions.

As in the case of the previous connectors, also the engagement connectors 60a, 60b, 61a, 61b, 62a, 62b, 63a, 63b are carried out as one piece with the main body 6.

Furthermore, all the aforesaid connectors are fastened to the peripheral wall 32, for instance on a free edge of said peripheral wall.

As can be seen in the section of FIG. 5, each engagement connector defines a gap leading towards the housing compartment 33.

Figure 7A:
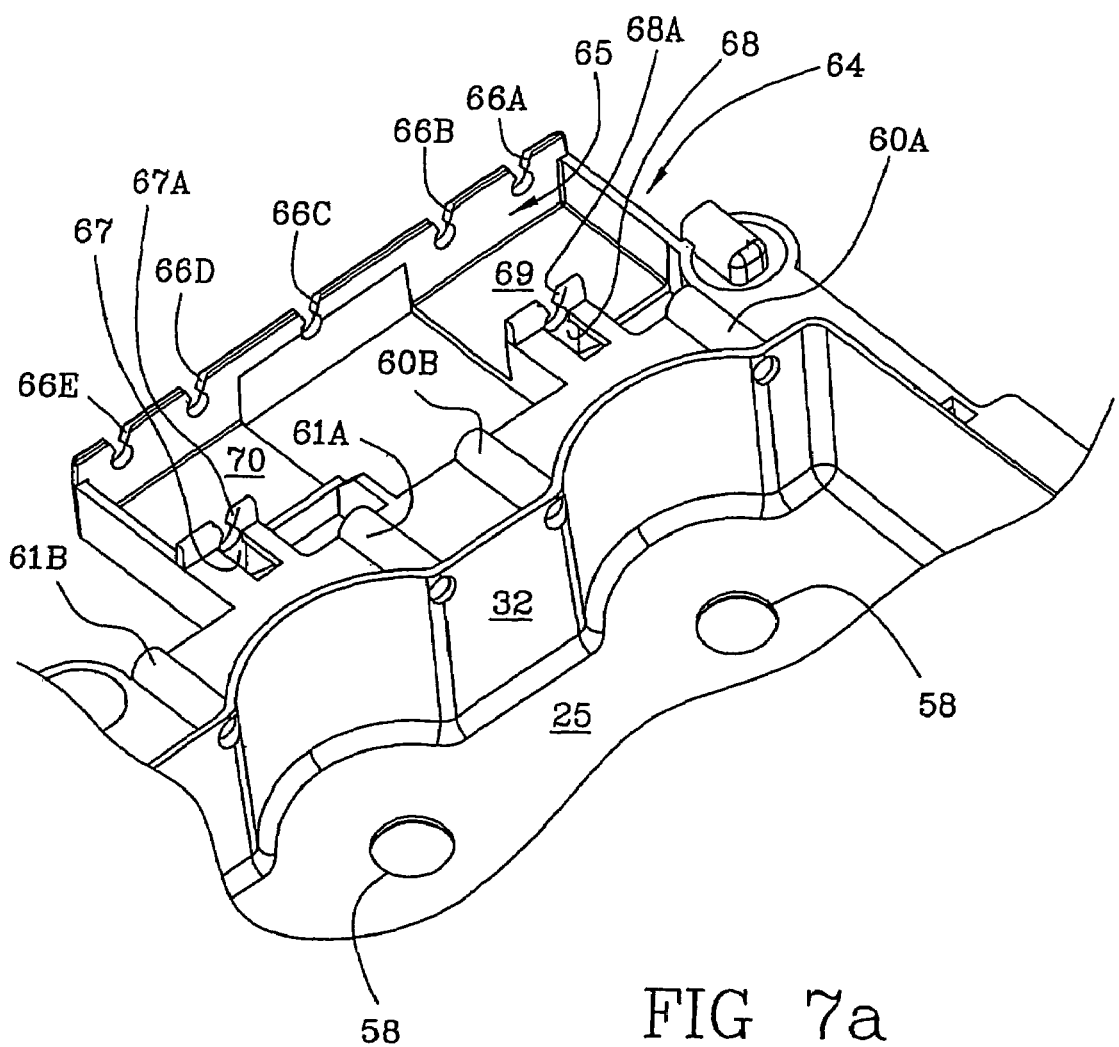
FIG. 7a shows an enlarged detail of the element of FIG. 7.
Figure 8A:
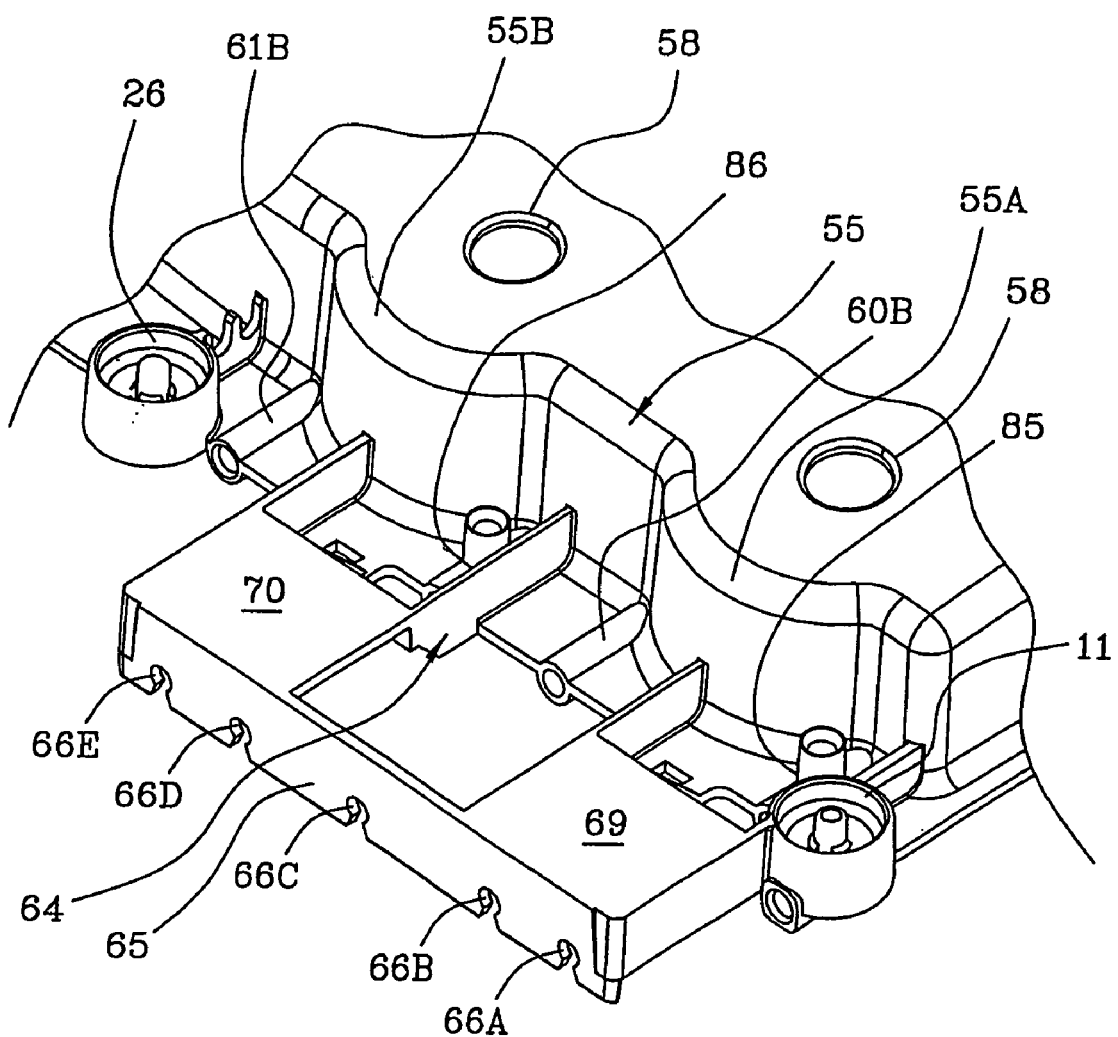
FIG. 8a shows an enlarged detail of the element of FIG. 8.

Referring now to FIGS. 7a and 8a, it can be noted how the support structure 64 associated to the main body 6 is positioned laterally with respect to the latter.

Also the support structure 64 is stiffly secured to the main body and will generally be carried out as one piece with the latter.

It should be pointed out that the support structure 64 is engaged to the main body 6 on one of the first longer sides 55, 56 and, in further detail, on the curved portions 55a, 55b of said fist longer side 55.

The support structure 64 is equipped with a positioning fin 65 (see again FIGS. 7a, 8a and the section of FIG. 6), which has a given number of main seats 66a, 66b, 66c, 66d, 66e suitably placed so that respective tubes of the fluid distribution circuit 15 associated to the support element 4 can be engaged therein.

Referring to the relative position of the various components of the support structure 64, it can be noted how at least two, and generally three of said main seats 66a, 66c, 66d are placed on their respective engagement connector 60a, 60b, 61a located near the curved portions 55a, 55b of one of the first longer sides 55.

Figure 9:
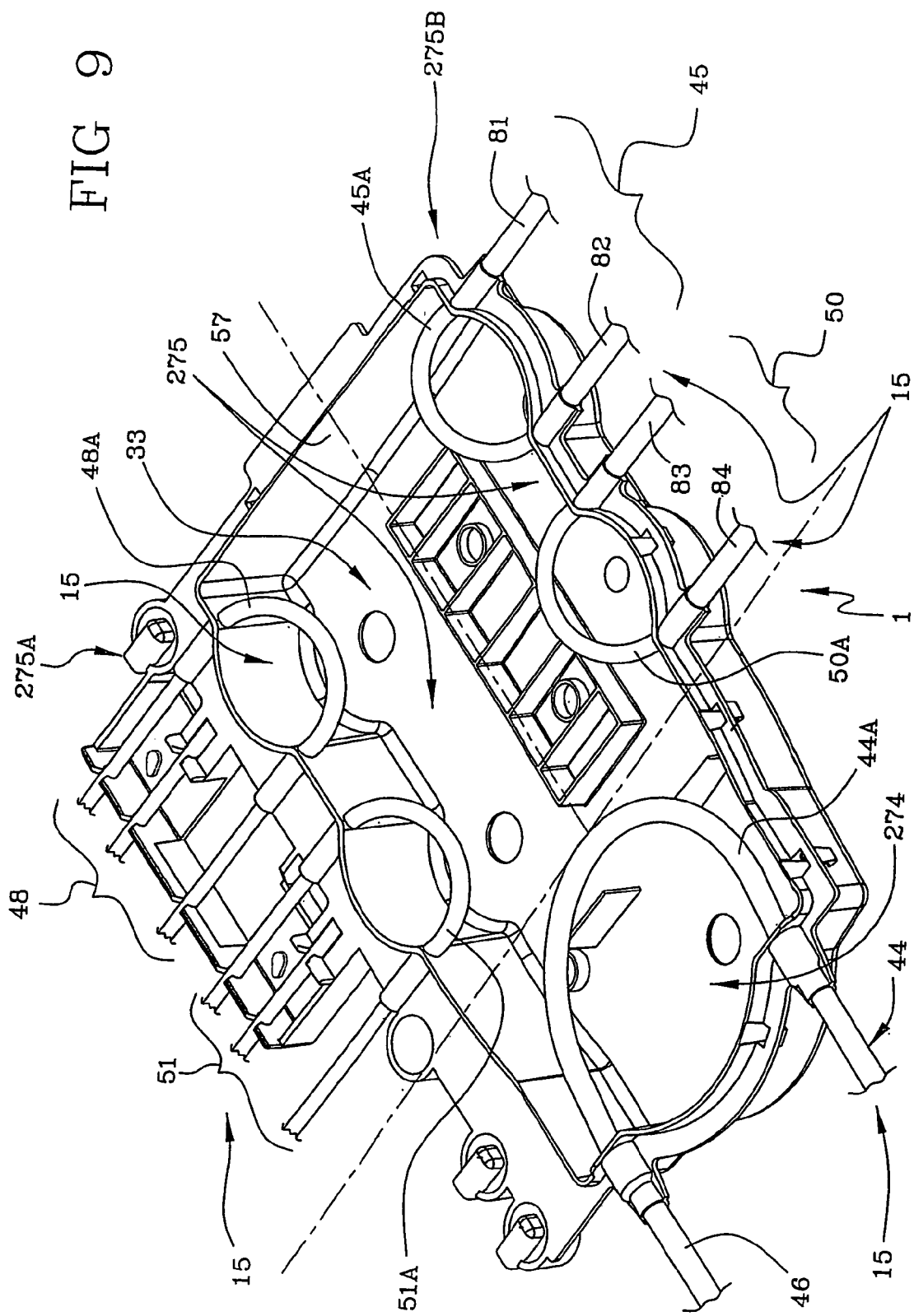
FIG. 9 shows a perspective view of an integrated module according to the present invention.

In other words, the three main seats 66a, 66c, 66d and their respective connectors 60a, 60b, 61a are positioned so as to receive parallel tube lengths (see to this FIGS. 9 and 9a).

Figure 6:
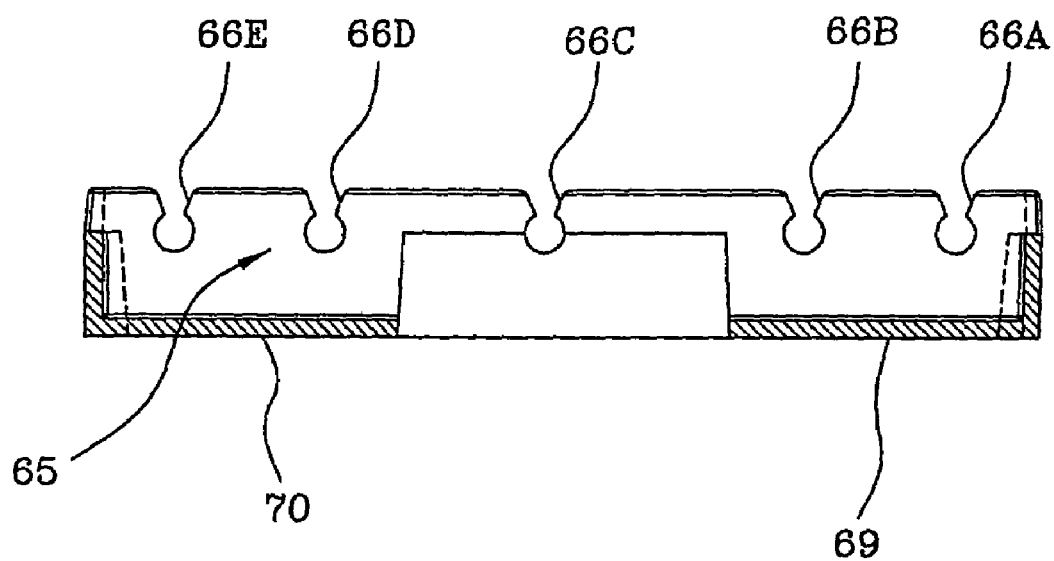
FIG. 6 shows a section according to line VI—VI of the support element of FIG. 2.

Going back to FIG. 6 and to FIGS. 7a and 8a, it can be noted how the positioning fin 65 comprises two further main seats 66b and 66e and how also the support structure 64 is equipped with two auxiliary portions 67 and 68, each of them being provided with a respective auxiliary seat 67a, 68a so that the latter can cooperate with one another thus enabling the positioning of tube lengths parallel one to the other and generally parallel to those present on the three main seats and on the three engagement connectors referred to above (see again FIGS. 9 and 9a).

The support structure 64 then comprises at least a first covering wall 69 lying on a plane parallel to the plane of the front wall 25 so as to cover at least two parallel tube lengths in operating conditions in which the support element is engaged to the machine.

Figure 16:
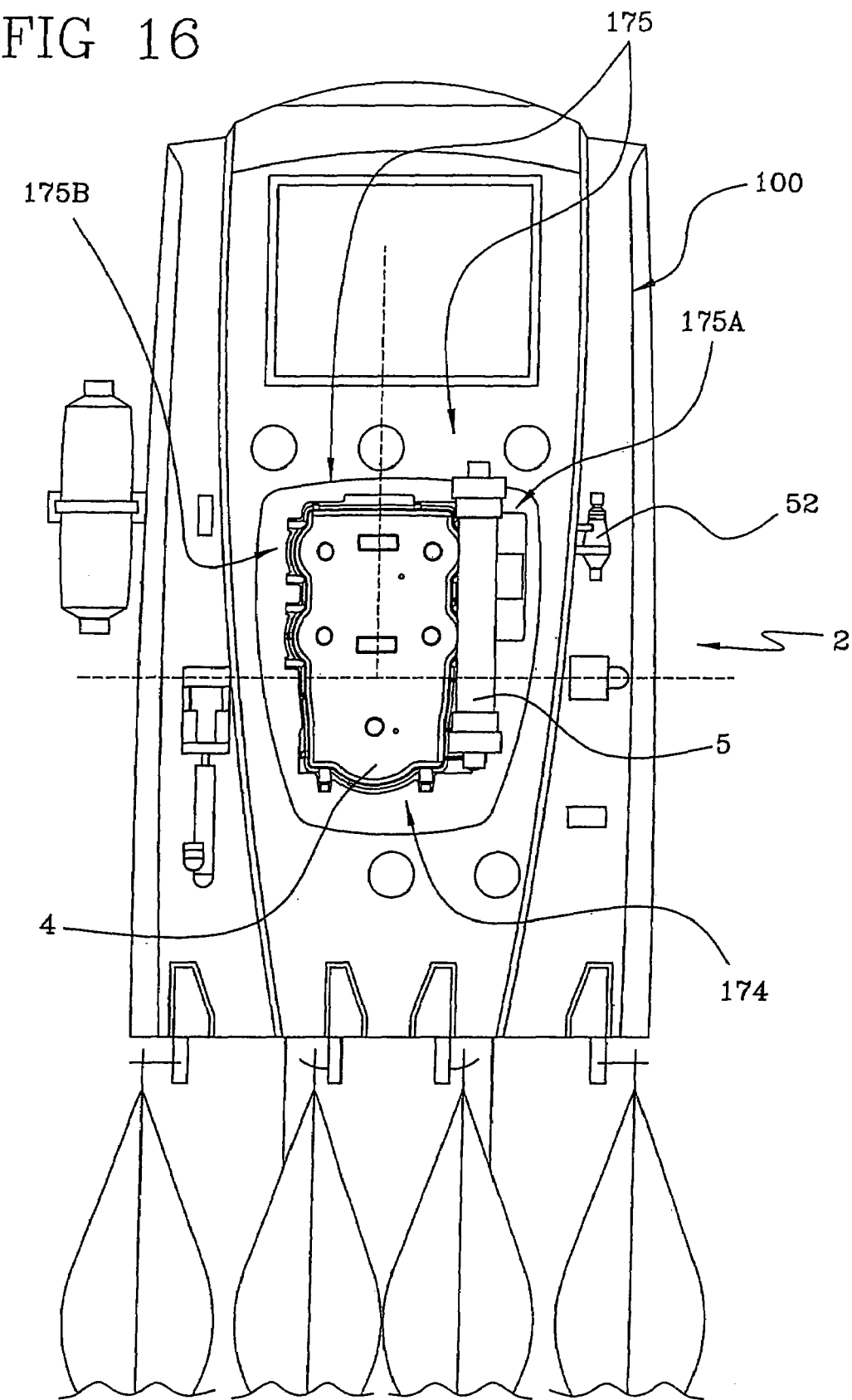
FIG. 16 shows a front view of the machine of FIG. 15 with an integrated module without the hydraulic circuitry thereto associated.

Compare to this FIGS. 9 and 16.

In a wholly specular way the support structure 64 comprises at least a second covering wall 70 lying again on a plane parallel to the plane of the front wall 25 so as to cover at least two further parallel tube lengths when the support element is again in operating conditions.

Referring to FIG. 8 it should then be pointed out that the support element 64 has a smaller height than—or at the most the same height as—the peripheral wall 32 of the main body.

This means that the support structure 64 has been designed so as not to increase the height of the whole support element.

Figure 14:
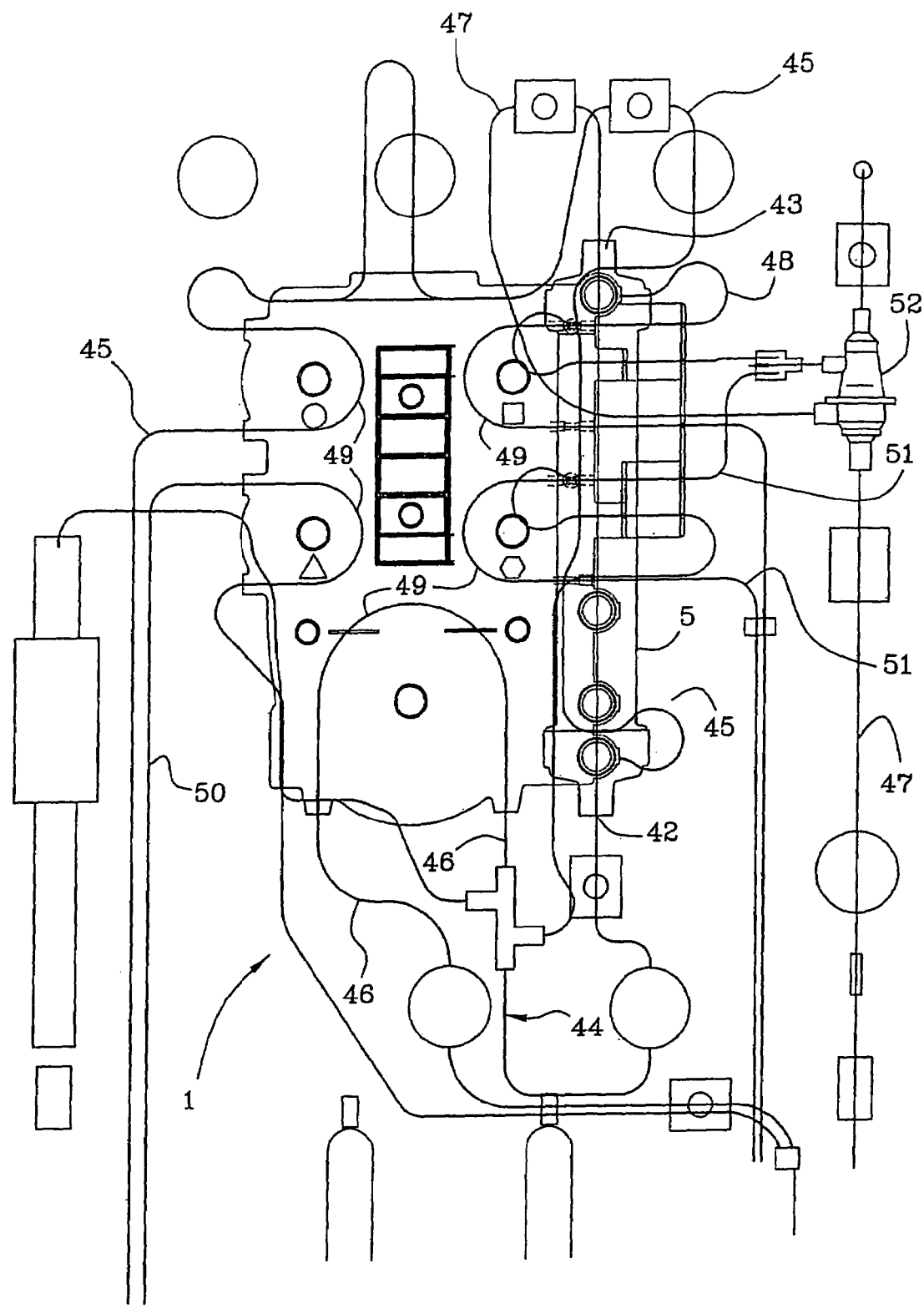
FIG. 14 shows a schematic view of the integrated module that can be associated to the machine, equipped with the hydraulic circuitry.

Referring now to FIG. 7, further note at least one and in generally two positioning projections 72 and 73 associated to the main body 6 and designed to enable the correct positioning of a tube length to be associated to the support element as shall be better explained later (see anyway FIGS. 9 and 14).

Said first and second positioning projections 72, 73 are placed inside the housing compartment 33 and are generally associated (or also carried out as one piece) to the front wall 25.

It should then be noted that the support element 4 comprises a main body 6 having at least a first and a second connector 7 and 8, spaced away from each other, in which corresponding counter-connectors 9 and 10 of the treatment unit 5 (see FIG. 11) are engaged.

The blood treatment unit 5 can for instance be a plasma filter, a haemodialysis filter, a haemofiltration filter, a haemodiafiltration filter or another type of unit.

The first and second connector 7 and 8 are directly engaged to the main body 6; in the examples shown said connectors are made of stiff plastic material and as one piece with the main body.

The support element 4 has a third connector 11 spaced away from the connectors 7 and 8 and engaged directly to the main body 6; in the examples shown also the third connector is made of stiff plastic material and as one piece with the main body; said three connectors define pairs of connectors having a differentiated central axis one with respect to the other for the engagement of corresponding pairs of counter-connectors associated to different blood treatment units that can be mounted onto the support element.

Thus, one main body 6 can be used to carry out integrated modules with different features., thanks to the possibility of engaging treatment units 5 not only with different membranes but also with different global size and therefore with different distance between central axis of the corresponding counter-connectors.

Each of the connectors 7, 8, 11 referred to is a stiff support and defines a fluid passage having a first end portion 12, designed to be put into fluid communication with a corresponding channel 13 present in the respective counter-connector 9, 10 housed in the treatment unit 5 (see also the sections of FIGS. 12 and 13); each connector 7, 8, 11 also has a second end portion 14, designed to be put into fluid communication with a fluid distribution circuit 15 to be associated to the main body 6.

Going into further structural detail, each of said connectors 7, 8, 11 comprises a tubular channel 16 defining said first portion, a sealing collar 17 placed radially outside the tubular channel, and a connection wall 18 developing without interruptions between an outer side surface 19 of the tubular channel and an inner side surface 20 of said collar.

In practice, the outer side surface of the tubular channel, the inner side surface of the sealing collar and the connection wall define a ring-shaped engagement seat 21, whose bottom is delimited by the connection wall, shaped so that a corresponding counter-connector of the treatment unit can be engaged therein.

The tubular channel 16 is arranged coaxially with respect to the sealing collar 17, and both turn around a common symmetry axis.

The ring-shaped seat 21 has an increasing radial size getting away from the bottom wall and comprises a first zone 22 near the bottom, having a constant radial size, a second zone 23, distal with respect to the bottom and with a constant radial size greater than the radial size of the first zone, and a third zone 24 between the first and the second zone, having a progressively increasing size getting away from the bottom wall 18.

The tubular channel and the sealing collar of each connector 7, 8, 11 project parallel one to the other from the main body 6, so as to define one direction of coupling with the corresponding counter-connectors of a treatment unit 5.

In the examples of embodiment shown the various connectors have a symmetry axis that is basically orthogonal with respect to a front surface 25 of the support element 4.

The support element shown also comprises a fourth connector 26 spaced away from said first, second and third connector; the fourth connector is also connected directly to the support element. In the example shown the fourth connector is made of stiff plastic material and as one piece with the main body 6 and defines with at least one of the other connectors a further pair of connectors associated to a blood treatment unit to be mounted onto the support element.

The fourth connector comprises a central cylindrical positioning body 27, a sealing collar 28 placed radially outside the cylindrical body, and a connection or bottom wall 29 developing without interruptions between an outer side surface 30 of the cylindrical body and an inner side surface 31 of said collar.

In practice, said fourth connector defines an engagement and flow-closing body for a counter-connector of the treatment unit 5.

Figure 11:
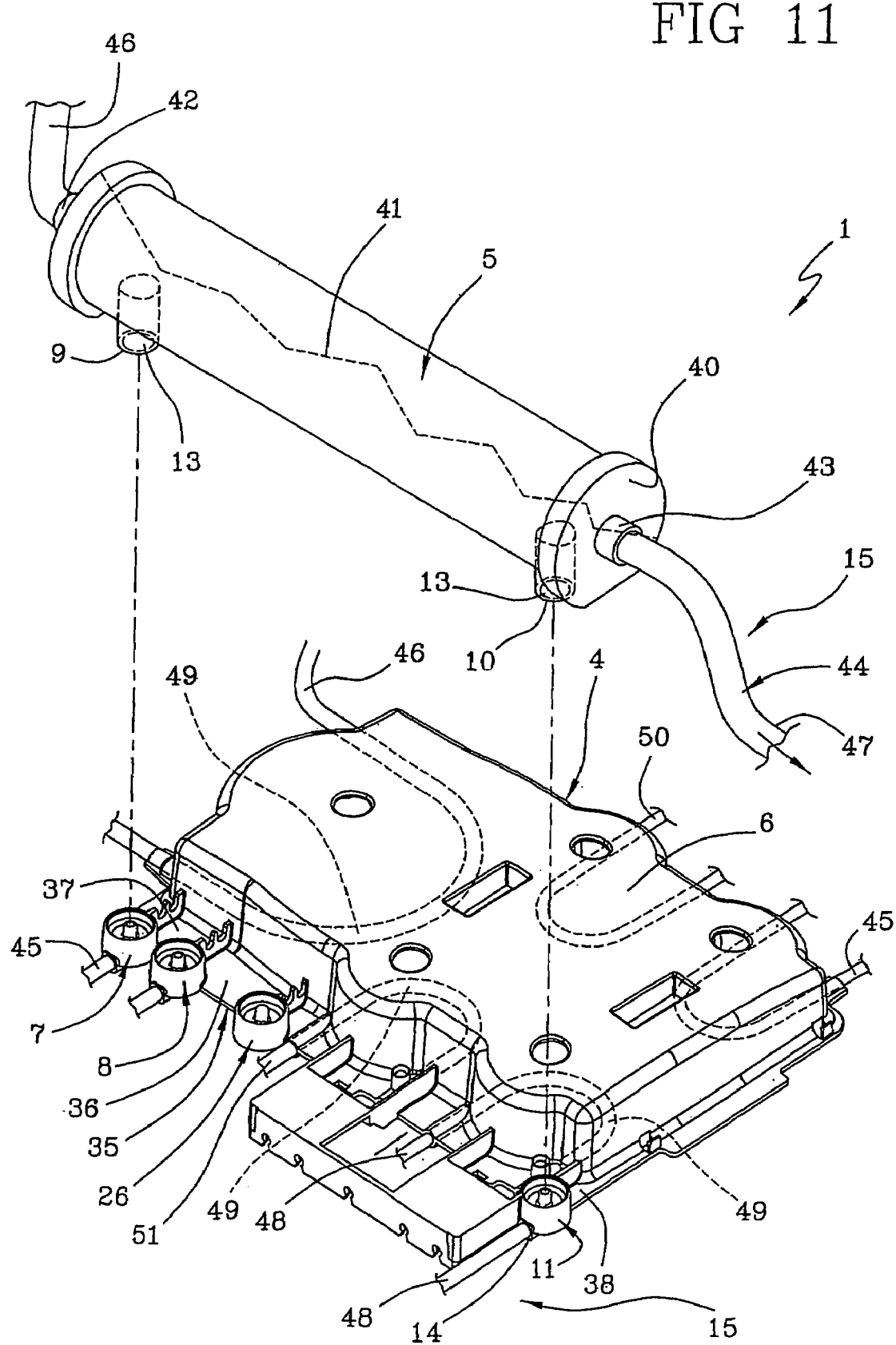
FIG. 11 shows the integrated module of FIG. 10 to which a blood treatment unit can be associated.
Figure 12:
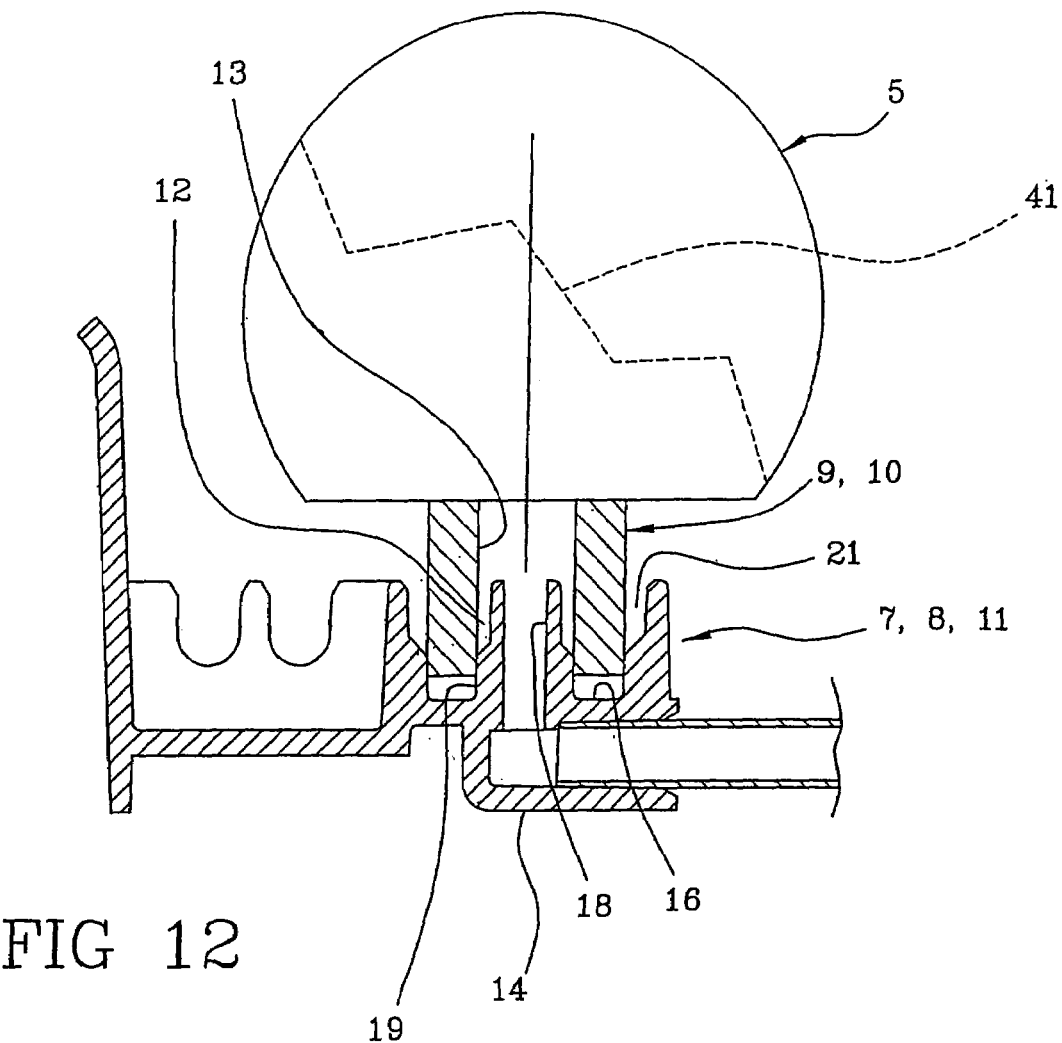
FIG. 12 shows a section of a connector of the support element and of a counter-connector of the blood treatment unit.
Figure 13:
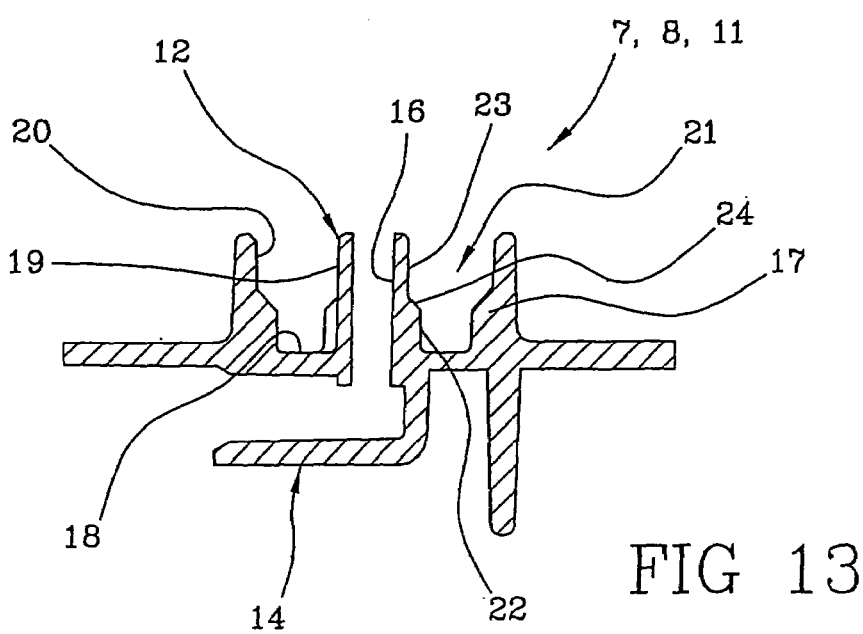
FIG. 13 shows a further section of a connector according to the present invention.

As shown in FIGS. 11, 12 and 13, the various connectors are made of stiff material so as to define a mechanical support of the treatment unit and, if needed, so as to define a passage or a blocking member for the fluid getting through the counter-connectors 9, 10.

The four connectors that are present in the support element are aligned one with respect to the other and arranged on one side of said main body.

More to the point, the main body of the element shown defines the aforesaid housing compartment 33, which can house at least a portion of the fluid distribution circuit 15 designed to be associated to the support element 4.

The housing seat has an open side 57 ensuring a suitable fitting and positioning of the integrated module 1 onto the machine 2, as shall be disclosed later in further detail.

The support element then has an auxiliary structure 35 extending laterally and outside with respect to the operating seat from a base zone 36 of the peripheral wall 32.

The four connectors come out from the auxiliary structure: the first, second and fourth connectors 7, 8, 26 are placed one beside the other and are arranged on a first end zone 37 of the auxiliary structure, whereas the third connector 11 is placed on a second end zone 38 placed opposite the first one.

Figure 10:
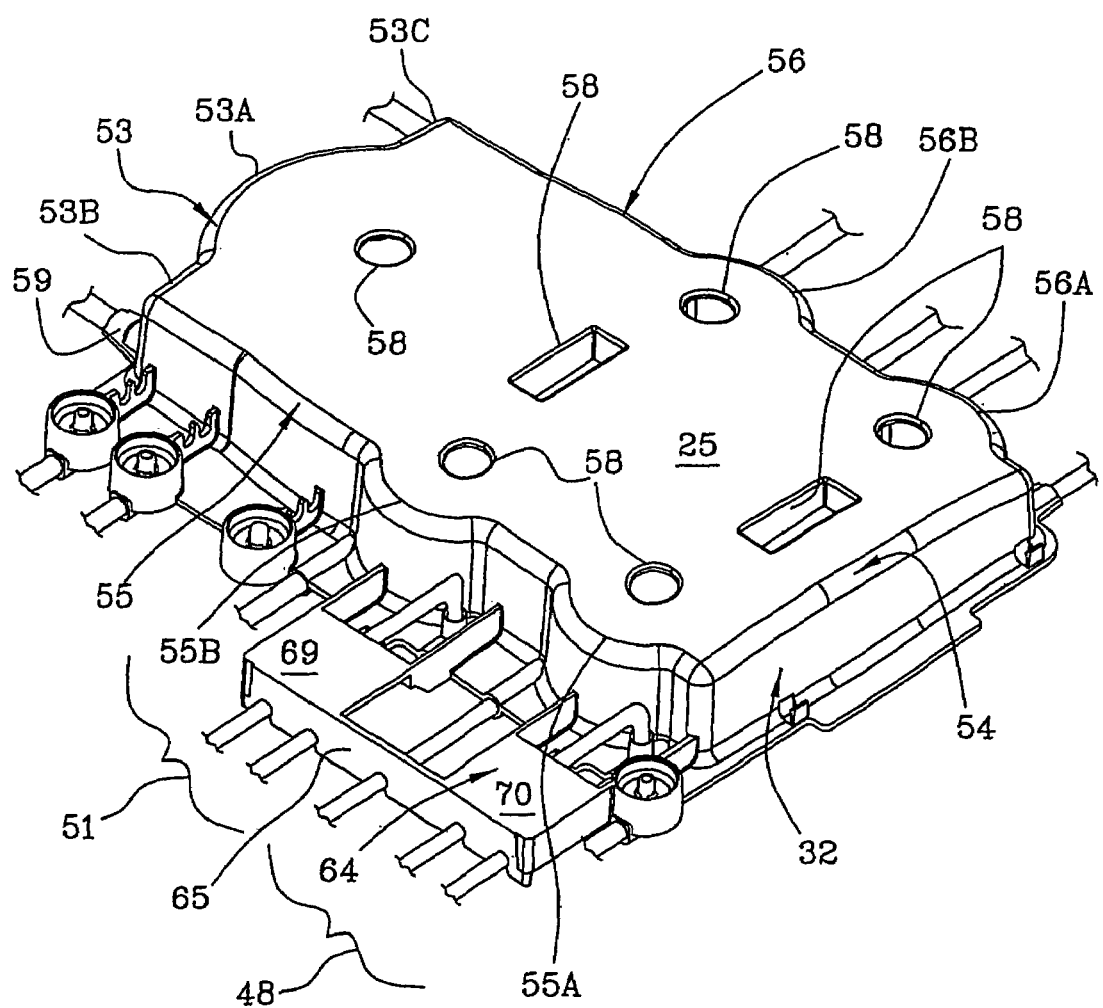
FIG. 10 shows a perspective view from the opposite side of the module of FIG. 9.
Figure 10A:
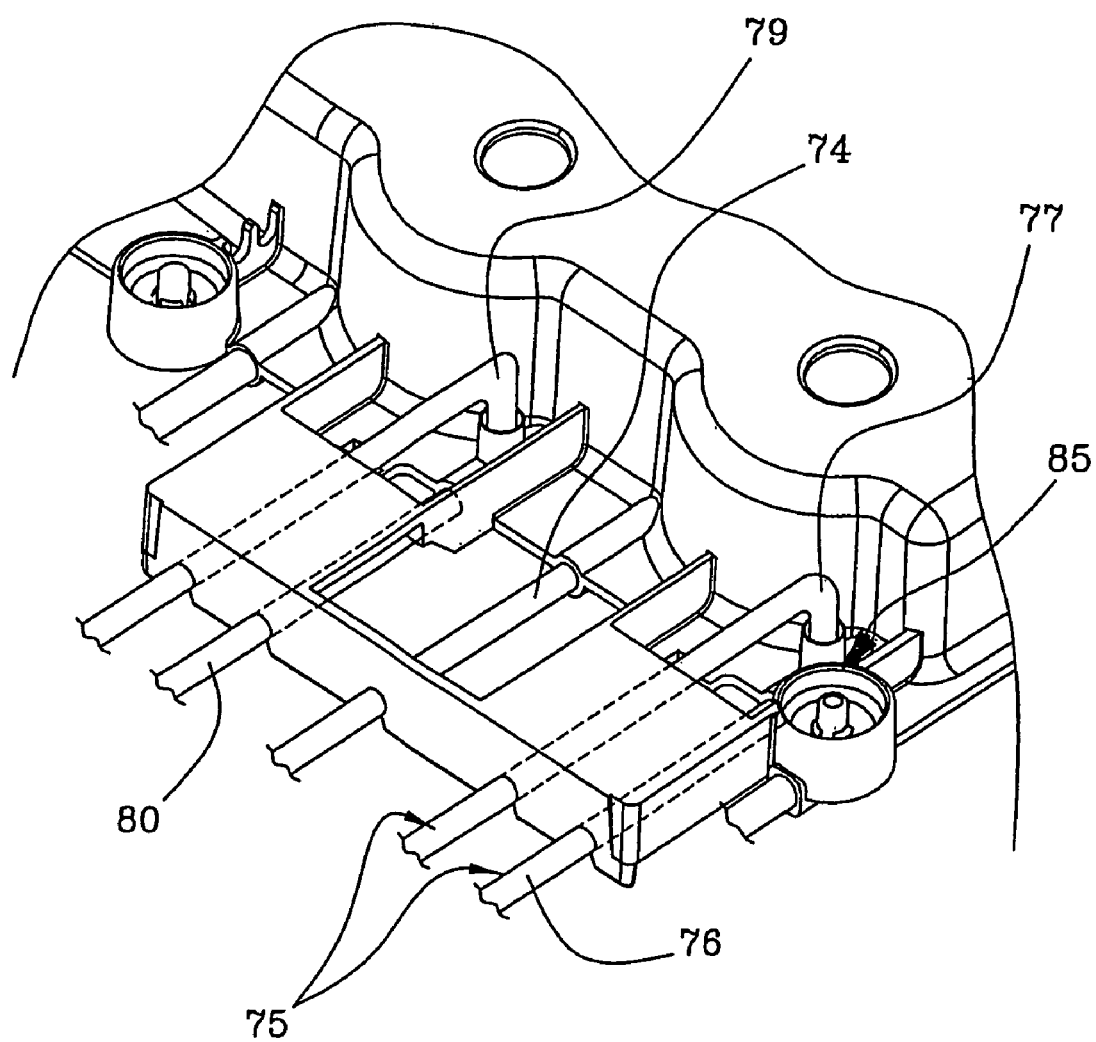
FIG. 10a shows an enlarged detail of the module of FIG. 10.

A support element according to the invention can be suitably used for carrying out an integrated module, such as for instance the one shown in FIGS. 9–11, in which the support element of FIGS. 2–8 is used by way of example.

As can be seen, the treatment unit 5 is fastened to the support element 4 on at least the pair of connectors; the treatment unit comprises a housing body 40, at least a semipermeable membrane 41 (for instance with parallel hollow fibers or with plates) operating inside the housing body and defining a first chamber and a second chamber; a first and a second counter-connector are associated to the housing body and secured to their respective connectors housed by the main body 6 (see for instance FIG. 11).

The first and second counter-connector 9, 10 have a tubular shape and are put into fluid communication with the second chamber of the treatment unit and with respective end portions 12 of said connectors.

The treatment unit then has an access door 42 leading to the first chamber, and at least an exit door 43 from said first chamber, for the connection with an extracorporeal circulation line 44 for blood or another physiological fluid.

A fluid distribution circuit 15 is engaged to the support element 4 and cooperates with the treatment unit 5.

In further detail said circuit comprises the aforesaid blood line 44, which is fastened to the support element 4 on one of the second sides 53, 54 and has the curved portion 53*a*.

The blood line 44 is secured to the support element so as to define at least a tube length basically arranged as a U 44*a* with respect to said support element.

Said arrangement is related to the fact of enabling the cooperation between said tube length 44*a* and a respective pump 3*a* while assembling the integrated module onto the machine 2.

As can then be inferred from the appended figures, the U-shaped tube length 44 extends inside with respect to the peripheral wall 32 of the support element 4.

The positioning projections 72, 73 previously described act on the U-shaped tube length 44*a* so as to keep its correct position.

As can be inferred from FIGS. 1 and 9, the length 44*a* of the blood line 44 secured to the support element is defined by the withdrawal branch 46.

The distribution circuit 15 then has the aforesaid inlet line 48 supplying fresh dialysis liquid.

Said line is fastened to the support element on one of the first longer opposite sides 55, 56, as can be seen in FIGS. 9, 9*a*, 10 and 10*a*.

Also the inlet line 48 is secured to the support element so as to define at least a tube length basically arranged as a U 48*a* with respect to said support element.

Also the tube length 48 is designed to cooperate with a respective pump 3*c* and is placed inside with respect to the peripheral wall 32 of the support element.

Referring to FIG. 9*a* it can be noted how the inlet line 48 is fastened to the main body 6 on the support structure 64, and how at least an inlet length 74 of the intake line 48 is engaged into a main seat 66*c* of the positioning fin 65, as well as to the respective engagement connector 60*b*.

Analogously, at least an outlet length 75 of the intake line is engaged into a main seat 66*a* of the positioning fin 65 and to the respective engagement connector 60*a*.

When engaged, the respective connectors and inlet and outlet lengths 74 and 75 are placed in a rectilinear arrangement and are parallel one to the other (see FIG. 9*a*).

As can further be seen (see in particular FIG. 10*a*), the outlet length 75 has a branching 85 splitting up into intake branch 76 conveying the fluid to the blood treatment unit 5, and into infusion branch 77 conveying the fluid into the blood line 44.

Said branching 85 is defined on the engagement connector 60*a* having a T shape with an inlet and two outlets.

Also the infusion branch 77 is secured to a main seat 66*b* and to an auxiliary seat 77*a*.

The infusion branch 77 and the intake branch 76, when engaged to the support structure 64, are placed in a rectilinear arrangement and are parallel one to the other.

The fluid distribution circuitry 15 then comprises at least the infusion line 51, which is also fastened on one of the first longer opposite sides 55, 56.

Said infusion line defines a tube length arranged as a "U" 51*a* with respect to said support element 4, so as to be able to cooperate, when in use, with a respective pump 3*d*.

Also the U-shaped tube length 51*a* extends inside with respect to the peripheral wall 32 of the support element.

Also the infusion line is secured on the support structure 64 and at least an outlet length 78 of the infusion line 71 is engaged into a main seat 66*d* of the positioning fin 65 and to its respective engagement connector 61*a* as shown in the appended figures.

In a wholly specular way to the intake line, the outlet length 78 has a branching 86 splitting up into pre-infusion branch 79 conveying the fluid to a withdrawal branch 46 of the blood line 44, and into post-infusion branch 80 conveying the fluid to a blood return branch 47 of the blood line 44.

Here again there is an engagement connector 61*a* having a T shape so that the branching 86 into pre-infusion branch 79 and into post-infusion branch 80 is defined exactly by said connector.

The pre-infusion branch 79 is then fastened to an auxiliary seat 68*a* and to a further main seat 66*e* of the positioning fin 65.

When engaged to the support structure, said two branches 79 and 80 are placed in a rectilinear arrangement and are parallel to one another.

The fluid distribution circuit 15 then has the discharge line 45 secured to the support element also on one of said first longer sides 55, 56.

Said discharge line 55 defines at least a tube length arranged as a U 45*a* with respect to the support element, which tube length is also designed to cooperate with a respective pump 3*b* and extends inside with respect to the peripheral wall 32 of the support element.

The discharge line 45 is secured to the main body 6 on an opposite side with respect to the support structure 64 and the respective inlet length 81 and outlet length 82 are engaged into corresponding engagement connectors 62*b*, 62*a*.

Eventually, the distribution circuit 15 has the auxiliary pre-infusion line 50.

The latter is fastened to the support element 4 on one of said first longer sides 55, 56 so as to define at least a further tube length arranged as a U 50*a* with respect to said support element.

Also the tube length 50*a* is designed to cooperate, when in use, with a respective pump 3*e* and extends inside with respect to the peripheral wall 32 of the support element.

In other words, the housing compartment 33 is designed to house all U-shaped tube lengths of the various lines of the distribution circuitry 15.

The auxiliary pre-infusion line 50 is secured to the main body on an opposite side with respect to the support structure 64 and the respective inlet length 83 and outlet length 84 are engaged to engagement connectors 63*b*, 63*a*.

It should then be pointed out that the particular shape of the peripheral wall 32 of the support element 4 defining the arched portions and the peculiar position of the engagement connectors of the various tubes result in that the length of every free U-shaped tube portion 44*a*, 45*a*, 48*a*, 50*a*, 51*a* is smaller than or the same as πR+2R, where R is the radius of curvature of the tube length.

The peculiar shape of the integrated module is such that the free lengths within the housing compartment 33 are as short as possible in accordance with the radial sizes of the respective pumps which have to generate the flow within said tubes.

It should then be noted how the U-shaped tube length 44*a* of the blood line is longer than the tube lengths 45*a*, 48*a*, 50*a*, 51*a* defined by the further fluid lines having indeed a longer radius of curvature.

Moreover, the tube length of the blood line can be carried out, if needed, with materials differing from those of other tubes and/or it can have sections for the passage of fluid differing from the other tubes.

From the point of view of the geometrical position of the various tube lengths on the support element note the following.

First of all, the support element can be ideally divided into a first zone 274 secured to the portion of the blood line 44 which, in operating conditions of the module 1 engaged to the machine 2, shall be defined by the lower zone of said module.

Therefore, there will be a second zone 275 opposite the first zone, to which all the further fluid lines 45, 48, 50 and 51 are secured.

Said second zone consists in its turn of at least two ideal half-parts placed side by side 275*a*, 275*b*.

The tube length 45*a* of the discharge line 45 and the tube length 50*a* of the auxiliary pre-infusion line 50 will be fastened to the second half-part 275*b*.

Conversely, the tube length 48 of the intake line and the tube length 51*a* of the infusion line are fastened to the first half-part 275*a*. Said splitting into first and second zone 274, 275 and the two half-parts 275*a*, 275*b* of the second zone have been ideally shown in FIG. 9 by means of hatched lines.

As can be noted, the first and second half-part 275*a*, 275*b* of the second zone 275 are reciprocally placed side by side and generally specularly symmetrical to a longitudinal axis of the main body 6.

Should the first zone 274 be geometrically delimited, it could be defined as the area limited by at least one of the second sides 53 (having the curved portion and to which the blood line is secured) and by about half the length of the first opposite longer sides 55 and 56 near the second side 53.

Analogously, the second zone 275 is partly delimited by one of said second sides 54 which has no curve and by a portion of the first opposite longer sides 55 and 56 near said second side 54.

The assembly process of an integrated fluid treatment module comprises the stage of installation of a support element 4, for instance as shown in FIGS. 2–8, and of a treatment unit 5 to be coupled to the support element.

Then the blood treatment unit is fastened to the support element.

Eventually, a fluid distribution circuit 15 is associated to the support element and to the treatment unit so as to create the necessary lines for blood circulation, discharge, infusion of possible substitution liquids, dialysis.

Note that the connection of the distribution circuit to the treatment unit can be before, simultaneous to or follow the stage in which the circuitry is fastened to the support element.

The stage in which the treatment unit is fastened to the support element comprises sub-stages in which a pair of connectors to which the counter-connectors 9, 10 housed by the blood treatment unit are to be fastened are chosen, in which a given amount of glue, normally based on a polymer resin, is placed in the ring-shaped seats 21 of each connector chosen, in which each counter-connector is at least partially fitted into its respective ring-shaped seat so as to obtain a mechanical blocking and a liquid-sealing coupling.

Note that during said fitting stage at least a portion of the glue placed in the ring-shaped seat reaches the second zone 23 of said ring-shaped seat.

At the end of said stage in which the counter-connector is fitted into its respective ring-shaped seat, the volume of glue previously placed plus the volume of the portion of counter-connector housed within the ring-shaped seat is smaller than the total volume of said ring-shaped seat. It is thus avoided that glue migrates towards the tubular channel 16 causing its partial or total occlusion.

The stage in which a fluid distribution circuit 15 is associated to the support element 4 and to the treatment unit 5 comprises in its turn the sub-stages in which an end portion of a discharge line 45 for a waste fluid is fastened fluid-sealingly with the second end portion 14 of one of said connectors, and in which an end portion of an intake line 48 for fresh dialysis liquid is fastened sealingly with the second end portion of another of said connectors.

Said stage of association of the distribution circuit also comprises the sealing fastening of an end portion of a blood withdrawal branch 46 with the inlet door to the first chamber, and an end portion of a blood return line 47 with the exit door from said first chamber.

The fastening of the various end portions referred to above can take place by gluing, by forcing or by hot coupling.

Figure 15:
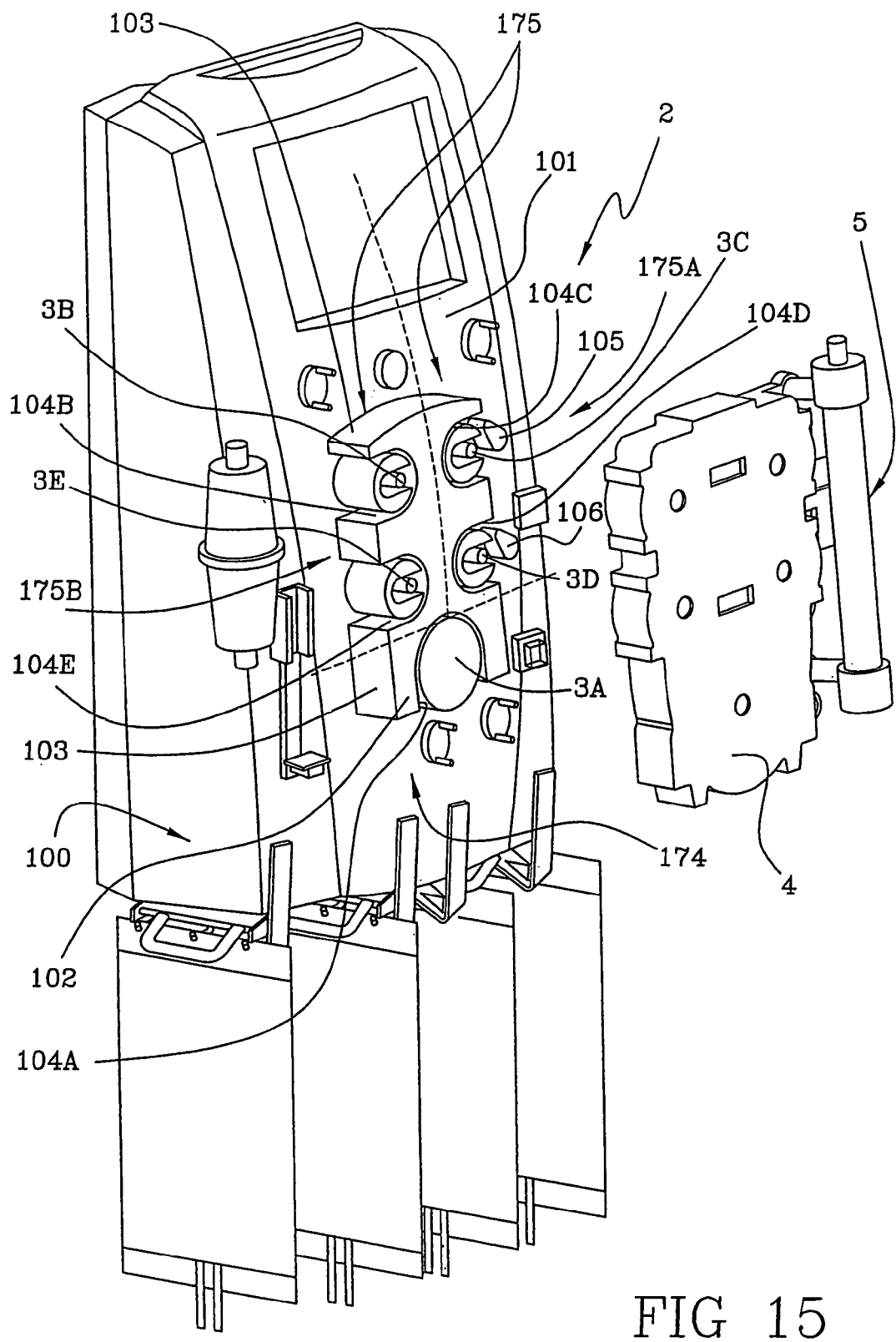
FIG. 15 shows a machine according to the present invention to which an integrated module can be associated.

Granted the above, it should be noted that the integrated module according to the present invention is designed to be used on an extracorporeal blood treatment machine 2 as shown in FIGS. 15 and 16.

In particular, said machine 2 comprises a body 100 provided on its front surface 101 with a given number of peristaltic pumps 3a, 3b, 3c, 3d, 3e designed to cooperate, when in use, with the respective U-shaped tube lengths defined on the integrated module.

As can be noted from FIG. 15, the machine body 11 has a guiding and positioning projection 102 protruding from the surface 101, which is exactly counter-shaped to the peripheral wall 32 of the support element to which it should be coupled.

In other words, the guiding and positioning projection 102 has a side surface 103 which, when engaged to the integrated module, is delimited by the peripheral wall 32.

Also the peristaltic pumps protrude from the surface 101 of the machine body 100 and at least a part of their side surface is counter-shaped to the peripheral wall 32 of the support element.

In particular, it is exactly the curved portions defined by the curved lengths of the front wall 25 which are designed to couple with the protruding side portions of the pumps 3.

The protruding peristaltic pumps and the guiding and positioning projection 102 define together suitable seats 104a, 104b, 104c, 104d and 104e taking a basically semicircular or U shape and designed to receive the corresponding U-shaped tube lengths 44a, 45a, 48a, 50a, 51a.

Analogously to what has been described for the integrated module 1, also on the front wall of the machine a given number of zones can be defined, and in particular two zones 174, 175 in which the first zone 174 comprises the blood pump 3a, whereas the second counterposed zone comprises the other pumps 3b, 3c, 3d and 3e.

The second zone 175 comprises at least two half-parts placed side by side 175a, 175b; the intake pump 3c and the infusion pump 3d are placed in said first half-part whereas the auxiliary pre-infusion pump 3e and the suction pump 3b are placed in the second half-part.

Here again the first and second half-part are specularly symmetrical and placed side by side on the front wall of the machine and above the first zone 174.

Eventually, it should be noted that there is at least a first moving element 105 and a second moving element 106 that are substantially identical and housed directly by the machine body; the latter are designed to act respectively on the infusion branch 77 and/or on the intake branch 76 (the first moving element), and on the pre-infusion branch 79 and/or on the post-infusion branch 80 (the second moving element 106). In particular, the selecting means 97 and 203 previously described can comprise said moving elements 105, 106 designed to be controlled by the CPU 209 so as to selectively determine the blocking or passage of fluid in either branch.

In order to cooperate with said moving elements the integrated module is equipped with the support structure with said infusion, intake, post-infusion and pre-infusion branches, which are all parallel to one another.

The invention has important advantages.

First of all, the shape of the support element allows to keep in their position the various tube lengths when the module is engaged to the extracorporeal blood treatment machine.

The peculiar C-shaped section of said element enables an optimal cooperation with the elements protruding from the front wall of the machine, so as to ensure an easy and correct engagement of said integrate module to the machine.

Furthermore, the presence of suitable seats counter-shaped to the U-shaped tube lengths enables an optimal positioning of the circuitry around the peristaltic pumps, thus highly reducing the possibility of mistakes made by the operators activating the unit.

It should then be noted that the box-like shape provides a substantial protection and covering for all the moving parts of the machine (we refer in particular to the peristaltic pumps and to the selecting elements for blocking/enabling the fluid flow in the respective tubes).

Moreover, the possibility of carrying out support element with transparent material enables a visual access, thus allowing to verify the correct positioning of the tube lengths with respect to their respective pumps, as well as the good working of the machine, though preventing a direct access to said parts.

Eventually, the relative arrangement of the various pumps and tube lengths ensures an efficient and easy access to the blood treatment element, and enables extracorporeal blood circulation lengths that are as small as possible.

The invention claimed is:

1. A support element for an integrated blood treatment module, comprising a main body having a front wall and at least a peripheral wall projecting away from said front wall, said front wall and said peripheral wall defining a housing compartment, said front wall being delimited by first and second opposite longer sides with a basically rectilinear development, each of said first and second opposite longer sides having first and second curved portions forming a cavity facing a respective opposite longer side, said front wall being further delimited by first and second opposite shorter sides with a basically rectilinear development, at least one of said first and second opposite shorter sides having a third curved portion configured between first and second rectilinear lengths, a cavity formed by said third curved portion facing the other of said first and second opposite shorter sides;

the support element further comprising at least one pair of tube engagement connectors, each of said at least one pair of tube engagement connectors being placed on opposite ends of each of said first, second, and third curved portions.

2. A support element according to claim 1, wherein the front wall is generally planar.

3. A support element according to claim 1, wherein the peripheral wall has at least a portion projecting away from each of said first and second opposite longer sides.

4. A support element according to claim 1, wherein the peripheral wall has at least a portion projecting away from each of said first and second opposite shorter sides.

5. A support element according to claim 1, wherein the peripheral wall projects away from said first and second opposite longer sides and said first and second opposite shorter sides of the front wall defining a basically continuous surface delimiting the housing compartment.

6. A support element according to claim 1, wherein each of said first, second, and third curved portions is defined by an arc of circle.

7. A support element according to claim 6, wherein the arc of circle defining the third curved portion has a greater radius of curvature than the arc of circle defining the first and second curved portions.

8. A support element according to claim 1, wherein the housing compartment has an access opening not having a closing wall, said access opening being configured to face a respective machine for extracorporeal blood treatment when the support element is being used.

9. A support element according to claim 1, wherein the main body has a substantially C-shaped profile sectioning a plane transverse to the front surface.

10. A support element according to claim 9, wherein the main body has at least two C-shaped sections orthogonal to one another, said at least two C-shaped sections configured to divide first and second planes, said first and second planes being orthogonal to one another and transversal to the front surface.

11. A support element according to claim 1, wherein the front wall has a given number of through openings putting the housing compartment in communication with an outside environment.

12. A support element according to claim 11, wherein at least one of said through openings is placed on each of said first, second, and third curved portions.

13. A support element according to claim 12, wherein each of said first, second, and third curved portions is defined by an arc of circle, said through openings placed on each of said first, second, and third curved portions being defined by round holes that are concentric with the respective arcs of circle.

14. A support element according to claim 1, wherein said front wall is at least partly transparent.

15. A support element according to claim 1, wherein said main body comprises a stiff material.

16. A support element according to claim 1, wherein said front wall and said peripheral wall define a main body having a box-shaped structure having six faces, said main body being substantially closed on five out of the six faces.

17. A support element according to claim 1, wherein at least one of said pairs of tube engagement connectors is fastened to said two rectilinear lengths of said at least one of said second opposite shorter sides.

18. A support element according to claim 1, wherein at least one of said pairs of tube engagement connectors is respectively secured near each of said first and second curved portions.

19. A support element according to claim 1, wherein said tube engagement connectors comprise a single piece with the main body.

20. A support element according to claim 1, wherein said tube engagement connectors are secured to said peripheral wall.

21. A support element according to claim 20, wherein said tube engagement connectors are secured on a free edge of said peripheral wall.

22. A support element according to claim 1, wherein each of said tube engagement connectors defines a gap, said gap facing the housing compartment.

23. A support element according to claim 1, wherein the support element further comprises a support structure associated to the main body, said support structure being placed laterally with respect to the main body.

24. A support element according to claim 23, wherein the support structure is firmly secured to the main body.

25. A support element according to claim 23, wherein the support structure comprises a single piece with the main body.

26. A support element according to claim 23, wherein the support structure is engaged to the main body on one of said first and second opposite longer sides.

27. A support element according to claim 26, wherein the support structure is engaged to the main body on said first and second curved portions.

28. A support element according to claim 23, wherein the support structure further comprises a positioning fin having a number of main seats configured to be engaged with respective tubes of a fluid distribution circuitry; said fluid distribution circuitry being associated to the support element.

29. A support element according to claim 28, wherein at least two of said main seats are placed on respective tube engagement connectors; said respective tube engagement connectors being placed near the first and second curved portions of one of the first and second opposite longer sides.

30. A support element according to claim 29, wherein said at least two main seats and the respective tube engagement connectors are configured to receive parallel tube lengths.

31. A support element according to claim 29, wherein the positioning fin comprises first and second further main seats, the support structure comprising first and second auxiliary portions, said first auxiliary portion being equipped with a first auxiliary seat, said second auxiliary portion being equipped with a second auxiliary seat, the first and second further main seats cooperating with respective first and second auxiliary seats so as to enable a positioning of first and second tube lengths, said first and second tube lengths being parallel to each other said first and second tube lengths also being generally parallel to tube lengths carried by said at least two main seats.

32. A support element according to claim 23, wherein the support structure comprises at least a first covering wall lying on a plane parallel to the plane of the front wall, said first covering wall being configured to cover at least two parallel tube lengths during operating conditions of the support element.

33. A support element according to claim 32, wherein the support structure further comprises at least a second covering wall lying on a plane parallel to the plane of the front wall, said second covering wall configured to cover at least two further parallel tube lengths during operating conditions of the support element.

34. A support element according to claim 23, wherein the support structure has a height smaller than or the same as a height of the peripheral wall of the main body.

35. A support element according to claim 1, wherein the housing compartment houses at least a portion of a fluid distribution circuitry configured to be associated to the support element.

36. A support element according to claim 1, wherein the support element further comprises at least one positioning projection associated to the main body; said at least one positioning projection being configured to enable a correct positioning of a tube length to be associated to the support element.

37. A support element according to claim 36 having at least first and second positioning projections, wherein said first and second positioning projections are configured inside the housing compartment, said first and second positioning projections being generally associated to the front wall.

38. A support element according to claim 1, further comprising at least first and second connectors associated to the main body, said first and second connectors being spaced away from one another and configured to be engaged with corresponding counter-connectors of a blood treatment unit, said corresponding counter-connectors being configured for mounting onto the support element.

39. A support element according to claim 38, wherein said first and second connectors are directly engaged to the main body.

40. A support element according to claim 39, wherein the first and second connectors comprise a single piece with the main body.

41. A support element according to claim 39, wherein said first and second connectors and said main body comprise a stiff material defining a mechanical support for said treatment unit.

42. A support element according to claim 39, wherein said first and second connectors are configured on one side of said main body.

43. A support element according to claim 38, further comprising at least a third connector spaced away from said first and second connectors, said third connector being directly engaged to the main body, said first, second, and third connectors defining pairs of connectors having a different distance between a central axis to engage corresponding pairs of counter-connectors associated to different blood treatment units, said corresponding pairs of counter-connectors being configured for mounting onto the support element.

44. A support element according to claim 43, wherein the third connector comprises a single piece with the main body.

45. A support element according to claim 44, wherein said first, second, and third connectors are not aligned with each other.

46. A support element according to claim 43, further comprising a fourth connector spaced away from said first, second and third connectors, said fourth connector comprising a single piece with the main body and defining, with at least one of the first, second, and third connectors, another pair of connectors to be engaged to a corresponding pair of counter-connectors associated to a blood treatment unit; said corresponding pair of counter-connectors being configured for mounting onto the support element.

47. A support element according to claim 46, wherein the fourth connector comprises:
a cylindrical central positioning body;
a sealing collar placed radially outside the cylindrical body; and
a connection wall developing without interruptions between an outer side surface of the cylindrical body and an inner side surface of said collar,
said fourth connector defining an engagement and flow-closing body for a counter-connector of the treatment unit.

48. A support element according to claim 43, wherein said first, second, and third connectors are aligned with each other.

49. A support element according to claim 38, wherein each of said first and second connectors defines a fluid passage having a first end portion configured for fluid communication with a corresponding channel present in the respective counter-connector carried by the treatment unit, each of said first and second connectors further defining a fluid passage having a second end portion configured for fluid communication with a fluid distribution circuit to be associated to the main body.

50. A support element according to claim 49, wherein each of said first and second connectors comprises:
a tubular channel defining said first end portion;
a sealing collar placed radially outside the tubular channel; and
a connection wall developing without interruptions between an outer side surface of the tubular channel and an inner side surface of the sealing collar, said connection wall defining a ring-shaped engagement seat for each of said corresponding counter-connectors.

51. A support element according to claim 50, wherein the tubular channel defining said first end portion is coaxially arranged with respect to the sealing collar, said ring-shaped seat having a bottom delimited by the connection wall.

52. A support element according to claim 51, wherein said ring-shaped seat has a radial size increasing away from the bottom.

53. A support element according to claim 52, wherein said ring-shaped seat has a first zone near said bottom, said first zone having a constant radial size, a second zone distal with respect to said bottom, said second zone having a constant radial size greater than the radial size of said first zone, and a third zone between the first and the second zone, said third zone having a size increasing progressively away from the bottom wall.

54. A support element according to claim 50, wherein the tubular channel and the sealing collar of each of said first and second connectors project parallel to one another from the main body defining one direction of coupling with the corresponding counter-connectors of a treatment unit.

55. A support element according to claim 38, wherein a support structure is associated to the main body, said first and second connectors and said support structure being configured laterally with respect to the main body on one of said first opposite longer sides.

56. A support element according to claim 55, further comprising an auxiliary structure extending laterally and outside with respect to an operating seat from a base zone of the peripheral wall, said first and second connectors projecting from the auxiliary structure.

57. A support element according to claim 1, wherein the support element is configured to be coupled, when in use, to an extracorporeal blood treatment machine.

* * * * *